(12) United States Patent
Brechot et al.

(10) Patent No.: US 6,210,962 B1
(45) Date of Patent: *Apr. 3, 2001

(54) NUCLEOTIDE AND PEPTIDE SEQUENCES OF AN ISOLATE OF THE HEPATITIS C VIRUS, DIAGNOSTIC AND THERAPEUTIC APPLICATIONS THEREOF

(75) Inventors: Christian Brechot; Dina Kremsdorf, both of Paris; Colette Porchon, Gentilly, all of (FR)

(73) Assignee: Institut Pasteur, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/201,912

(22) Filed: Nov. 30, 1998

Related U.S. Application Data

(63) Continuation of application No. 07/965,285, filed as application No. PCT/FR92/00501 on Jun. 4, 1992, now Pat. No. 5,879,904.

(30) Foreign Application Priority Data

Jun. 6, 1991 (FR) .................................. 91 06882

(51) Int. Cl.$^7$ .................................. C07H 21/04
(52) U.S. Cl. ................. 435/320.1; 435/69.3; 435/235.1; 536/23.72
(58) Field of Search ............................ 435/320.1, 69.1, 435/69.3, 252.3, 235.1; 536/23.72, 23.1

(56) References Cited

U.S. PATENT DOCUMENTS 5,350,671  9/1994  Houghton et al. .

FOREIGN PATENT DOCUMENTS

| 0 318 216 | 5/1989 | (EP) . |
| 0 398 748 | 11/1990 | (EP) . |
| WO/8904669 | 6/1989 | (WO) . |
| WO 90/00597 | 1/1990 | (WO) . |
| WO 90/11089 | 10/1990 | (WO) . |
| WO 92/21759 | 2/1992 | (WO) . |

OTHER PUBLICATIONS

Okamoto et al., "The 5'–Terminal Sequence of the Hepatitis C. Virus Genome," *Japan J. Exp. Med.,* 60, 3, pp. 167–177 (1990).

Weiner et al., "Variable and Hypervariable Domains are Found in the Regions of HCV Corresponding to the Flavivirus Envelope and NSI Proteins and the Pestivirus Envelope Glycoproteins," *Virology,* 180, pp. 842–848 (1991).

Choo et al., "Isolation of a cDNA Clone Derived from a Blood–Borne Non–A, Non–B Viral Hepatitis Genone," *Science,* 244, pp. 359–362 (1989).

*Primary Examiner*—Laurie Scheiner
(74) *Attorney, Agent, or Firm*—Finnegan, Henderson, Farabow, Garrett & Dunner, L.L.P.

(57) ABSTRACT

This invention relates to oligonucleotides encoding HCV E1 peptides, labeled oligonucleotide probes, recombinant DNA molecules comprising HCV E1 nucleotides, plasmid, expression vectors and transformed hosts.

3 Claims, 19 Drawing Sheets

```
1  CCATGGCGGTTAGTATGAGTGTCGTACAGCCCTCCAGGACCCCCCTCCCGGAGAGCCATA  60
2  ..........................G.................................  60
3  ..........................G.................................  60
4  ..........................G.................................  60

1  GTGGTCTGCGGAGCCGGTGAGTACACCGGAATTGCCAGGACGACCGGGTCCTTTCTTGGA  120
2  ...........A.................................................  120
3  .............................................................  120
4  ...........A.................................................  120

1  TCAACCCGCTCAATGCCTGGAGATTTGGGCGTGCCCCCGCAAGACTGCTAGCCGAGTAGT  180
2  .A..........................................C.........G....  180
3  .A..........................................C..............  180
4  .A..........................................C.........G....  180

1  GTTGGGTCGCGAAAGGCCTTGTGGTACTGCCTGATAGGGTGCTTGCCGAGTGCCCCGGAG  240
2  .............................................................  240
3  .............................................................  240
4  .............................................................  240

1  GTCTCGTAGACCGTGC  256
2  ................  256
3  ................  256
4  ................  256
```

FIG. 2

```
1   TTCTGGAAGACGGGGTGAACTATGCAACAGGGAACCTTCCTGGTTGCTCTTTCTCTATCC    60
2   ............................................................    60
3   .................G..........................TT.G.C.........T   60
4   ............................................................T   60
5   .................G..........................T.G.C.........T   60

1   TCCTCCCTGCTCTCTTGCCCTGACTGTGCCCGGGTCAGCCTACCAAGTACGCAATT       120
2   ....T..................T............T.G.....G..........       120
3   ....T......G..C..TT....CA.C..A..T..C..T..TG.....G......CG      120
4   ...........................T........T.C..................C.   120
5   ....T......G..C..TT....CA.C..A..T..C..T..TG.....G......CG     120

1   CTCGCGGCCCTTTACCATGTCACCAATGATTGCCCTAACTCGAGTATTGTGTACGAGACGG   180
2   .CACG..G...........C...............................G.......   180
3   TGTC...GA.A.........A..C..C..T.C....A.C.....T...G.........   180
4   .CACA..G....T..........G.C..T.C..........A.C............G.C.   180
5   TGTC...GA.A.........G.C..T.C....A.C.....T...G.A.           180

1   CCGATAGCCATTCTACACTCTCCGGGGTGTGTCCCTTGCCGTTCGGCGAGGGTAACACCTCGA 240
2   ....GC..C..G..A..........................C.........T..C..G...... 240
3   .G..CGTG..CA.G..TG.C..C.........C..G..C..G..AAC..TT....CC  240
4   .A...GC..C..G..TA.............C........................C..GT...... 240
5   .G..C.TG..CA.G..TA.............C........................AC....G...CC 240
```

FIG. 3A

```
   AATGTTGGGTGGCGGGTGGCCCCCTACAGTCGCCACCAGAGACGGCAGACTCCCCACAACGC   300
1  GG........A..A......G..G......G..T..A..........G.G............   300
2  GT..C....A...C.CA.T.C..GC.....GG...GA.T.C...CG........T..A....   300
3  GG........A..A......G.G.......G...A..........G.G.............   300
4  GT..C....A...C.CA.T.C..GC.....GG...GA.T.C...CG........T..A....   300
5

AGCTTCGACGTCATATCGATCTGCTCGTCGGGAGCGCCACCCTCTGCTCGGCCCTCTATG     360
1  ..........C...CG......T.......T......CG..TG.TT.....C..TA.G..C.   360
2  CAT.A....C...CG......CT..........T........CG..TG.TT.....C..TA.G..C.   360
3  ..........C...CG......T.......T......GCG..TG.TT.....C..TA.G..C.   360
4  CAA.A....C...CG......CT..........T........CG..TG.TT.....C..TA.G..C.   360
5

TGGGGGACTTGTGCGGGTCCGTCTTCCCTCGTCGGTCAATTGTTCACCTTCTCCCCCAGGC    420
1  ..C.A.......T..T.T..C...........T.........T............         420
2  ....TC.C....A.T..T....A.TCC..GC...............G..TC.C........   420
3  ..TC..............TA.T...C..T...........T.................    420
4  ....TC.C....A.T..T....A.TCC..GC...............G..TC.C........   420
5

GCCACTGGACAACGCAAGACTGTTCCATCTACCCCGGCCACGTAACGGGTCACC            480
1  .....G......GT..T.C.T..T.........TA.........               480
2  .G..TGA....GTA..G.....G....C..A....T......TA....T.A..C..T..    480
3  .............G.........T.......T.........            480
4  .G..TGA....GT...G.....G....C..A....T......TA....TT.T.A..     480
5
```

*FIG. 3B*

```
1  GCATGGCATGGGATATGATGA    501
2  ....................    501
3  .........T..........    501
4  ....................    501
5  .............T......    501
```

FIG. 3C

```
1   LEDGVNYATGNLPGCSFSILLALLSCLTVPASAYQVRNSRGLYHVTNDCPNSSIVYETA    60
2   ....................F.................T.................A.   60
3   .A.................F..........I..E...VS.I.....S.........A.   60
4   ....................F.................T.................AH  60
5   .A.................F..........I..E...VS.I.....S.........A.   60

1   DSIHSPGCVPCVREGNTSKCWVAVAPTVATRDGRLPTTQLRRHIDLLVGSATLCSALYV  120
2   .A..T........A.R....MT........A.....T.V.......T.AF.....M..  120
3   .V.M.A.......N.S.R..LT..L.A.NASV....T.V.......T.AF.....M..  120
4   .A..T........V.R....MT........A.....TI.V......A.AF.....M..  120
5   .M.M.T.......D.S.R..LT..L.A.NASV....TI.V......A.AF.....M..  120

1   GDLCGSVFLVGQLFTFSPRRHWTTQDCNCSIYPGHVTGHRMAWDMM              166
2   ...........IS................G........I......              166
3   ..........I................E.V.........S.....              166
4   ............................G........I......              166
5   ...........S................E.V.......LS.....              166
```

```
1  GATCAACACCAACGGCAGCTGGCACATTAATCGCACAGCTTTGAACTGTAATGAGAGCCT  300
2  ..............T...........C.C..A...G..CC.....C........T...  300
3  ..............T.................C....G..C.....C........A..  300
4  TG.G..T...............C..CA.G..T..CC.A........C......CTC..  300
5  TG.A..........T.....T........T..C..CA.G..T..CC.........CTC...  300

1  CGACACCGGCTGGGGTAGCGGGCTCTTCTATTACCACAAATTCAACTCTTTCAGGCTGCCC  360
2  TA........T.G.A......T....C........G..................T....  360
3  TA........T.G.A......TA...C.A.......................G..T...  360
4  .C....T.G.TCC.T..C.C..G.......CACA.....GG........G.C..G.....  360
5  .C.A..T.G.TCC.T..C.C...G                                       325

1  CGAGAGGATGGCCAGCTGCAGACCCCCTTGCCGATTTCGACCAGGGCTGGGGCCCTATCAG  420
2  T......C.A..................C......A....T..................  420
3  ......T.....................C..G..A....T..................  420
4  G..C.C............C.C..A..A.TGG....C.....A............C      420
5                                                                 325

1  TTATGCCAACGGAACCGGCCCTGAACACCGCCCCTACTGCTGGCACTACCCCCCAAAGCC  480
2  ..........G.....G.....C..C..G..................A...          480
3  .C........G.....G.....C..C..A.............T.T.........A...   480
4  C...A.TG.GCCTGA.A.....G.T..GA.G..T..T............T...G.G..TCGA..  480
5                                                                 325
```

```
1   TTGTGGTATCGTGCCAGCACAGACCCGTATGTGGCCAGTGTATTGCTTCACTCCCTAGCCC   540
2   ....T........C..GA...GT..G.....T.G..A.......C...........      540
3   ....C........C..A....G.........G..A.........C...........      540
4   .............C........A..C....GTC.CAG..G......T.........      540
5   G............A..C...GTC.CAG..G......T....C..A...........      325

1   CGTGGGTGGGGACGACCAATAAGTTGGGCGCACCCACTTACAACTGGGGTTGTAATGA    600
2   ................A........G.C.G..C.......G................   600
3   ................A................C......G...........GAA.   541
4   .......T.................................................   541
5   .........................................................   325

1   TACGGAGACGTCTCTTCGTCCTTAATAACACCAGGCCACCGCTGGGCAATTGGTTCGCTGCAC    660
2   ...............................C.T.......................T.. .   660
3   .............................................................   541
4   .............................................................   541
5   .............................................................   325

1   CTGGGGTGAACTCATCTGGATTTACTAAAGTGTGCCGAGCCCTCCCTGTGTCATCGGAGG    720
2   ......A.......A......C..C.................T.................   720
3   .............................................................   541
4   .............................................................   541
5   .............................................................   325
```

FIG. 5C

```
1   AGCGGGCAATAACACCTTGTACTGCCCCACTGACTGTTTCCGCAAGCATCCGGAAGCTAC    780
2   G..........C.........C..C................T.C..........C..C..    780
3                                                                 541
4                                                                 541
5                                                                 325

1   ATACTCCCGATGTGGCTCCGGTCCCTTGGATCACGCCCAGGTGCCTGGTTGGCTATCCTTA    840
2   .......T..G..C................C..................C.A...C..G.    840
3                                                                 541
4                                                                 541
5                                                                 325

1   TAGGCTCTGGCATTATCCCCTGTACTGTCAACTACACCCTGTTCAAGGTCAGGATGTACGT    900
2   ........T............T...CA..............A.A..T..AA.........    900
3                                                                 541
4                                                                 541
5                                                                 325

1   GGGAGGGGTCGAGCACAGGCTGCAAGTCGCTTGCAACTGGACGCGGGGCGAGCGTTGTAA    960
2   ..........A..........G...CT..C.................A......CG..    960
3                                                                541
4                                                                541
5                                                                325
```

FIG. 5D

```
1  TCTGGACGACAGGGACACAGGTCCGAGCTCAGTCCGCTGCTGCTGTCTACCACACAGTGGCA  1020
2  ..........A.................................................  1020
3  ............................C...T.A......A.C..T............   541
4  ............................................................  541
5  ............................................................  325

1  GGTCCCTCCCGTGTTCCTTTACGACCTTGCCAGCCTTGACTACCGGCCCTCATCCACCTCCA  1080
2  ............................................................  1080
3  .............................C..A......C.A......T.C........   541
4  ............................................................  541
5  ............................................................  325

1  CCAGAACATCGTGGACGTGCAATATATTTGTACGGGGTCAAGCATTGTGTCCTGGGC      1140
2  ..........................................................    1140
3  ...........T.............G..C...................C.C......     541
4  ..........................................................    541
5  ..........................................................    325

1  CATCAAGTGGGAGTACGTCATTCTCCCTGTTTCTCCTGCTTGCAGACGCGGCGGTCTGCTC  1200
2  ............................................................  1200
3  ....T................G................C..T.................   541
4  ............................................................  541
5  ............................................................  325
```

*FIG. 5E*

```
1                                          1210
2  CTGCTTGTGG . . . . . . . . . . .        1210
3                                           541
4                                           541
5                                           325
```

```
1  AGNNTLYCPTDCFRKHPEATYSRCGSGPWITPRCLVGYPYRLWHYPCTVNYTLFKVRMYV  300
2  .........H.......D..........................I...I........  300
3  ..........................................................  180
4  ..........................................................  180
5  ..........................................................  108

1  GGVEHRLQVACNWTRGERCNLDDRDRSELSPLLLSTTQWVLPCSFTTLPALTTGLIHLH  360
2  ....EA..........D.E..............T.....................S.  360
3  ..........................................................  180
4  ..........................................................  180
5  ..........................................................  108

1  QNIVDVQYLYGVGSSIVSWAIKWEYVILLFLLLADARVCSCLW  403
2  .............A..............V..............  180
3  ............................................  180
4  ............................................  180
5  ............................................  108
```

FIG. 6B

```
1  ACAATACGTGTGTCACCCAGACAGTCGACTTCAGCCCTTGACCCTACCTTCACCATTGAAA   60
2  ..........................T.................................G.   60
3  ..GT..C..A..........T.....G......T......TG.T..C..TC.......C..G.   60

1  CAACAACGCTTCCCCCAGGATGCTGTCTCCCGCACTCAACGTCGGGGCAGGACTGGCAGGG  120
2  ...TC....C.................................................   120
3  ..G..G..CG.G......A......G..T.G......G...G..G..A..T.........   120

1  GGAAGCCCAGGCATTTACAGATTTGTGGCACCTGGAGAGCGCCCCTCCGGCATGTTCGACT  180
2  ........................C..............G..G................   180
3  .C.G.AG..........C...T.G......A.T..A.....A..G.....G..CG.....   180

1  CGTCCGTCCTCTGCGAGTGCTATGACGCAGGCTGTGCTTGGTATGAGCTCACGCCCGCCG   240
2  .....................T.......................T..........   240
3  ..T..G....A..T..........G................T.............   240

1  AGACCCACAGTCAGGCTACGAGCATACATGAACACCCCGGGACTTCCCGTGTGCCAAGACC  300
2  .............................G............G..........C.....   300
3  ......T..T..T..T.G.T..C.A.T..A..GT.G.........C........G.....   300
```

FIG. 8A

```
1  ATCTTGAGTTTTGGGAGGGGCGTCTTCACGGGTCTCACCCATATAGAGCGCCCACTTCCTAT    360
2  ......A.................T.A..C....T........T.....T......         360
3  .......G...C.....A...........A..C.......C..........T.G.          360

1  CCCAGAGACAAAGCAGAGAGTGGGGAAAACCTTCCTTACCTGGTAGCGTACCAAGCCACCGTGT   420
2  ........................G.........................              420
3  ......T....GCA..A..C...T.C..C......A......                        420

1  GCGCTAGGGCCCAAGCCCTCCCCCCGTGGGACCAGATGTGGAAGTGCTTGATTCGTC         480
2  ...............T...........A...........T......C..                480
3  .....C....TA.G..T..A......T..A..........TC.C..A..G..              480

1  TCAAGCCCCACCCTCCATGGGCCAACACCCCTGCTATACCGACTGGGCGCTGTTCAGAATG    540
2  .............................A..................                540
3  ..A....T..G..G..C........G........G..TA.G..A..A..C..C..          540

1  AAGTCACCCTGACGCACCCAATCACCAAATATATCATGACATGTCGGCTGACCCTGG        600
2  ..A.....................G................C..                     600
3  ..G.......C..A.....T.A.......                                     569
```

*FIG. 8B*

```
1  AGGTCGTCACGAGTACCTGGGGTGCTCGTGGGCGGCGTTCTGGCTGCTTTGGCCGGCGTATT  660
2  .....................C.................T.................C..  660
3  ............................................................  569

1  GCCTATCCACAGGCTGCTGGTGGTCAGGGTCATTTGTCCCGGGAAGCCGGCAA  720
2  ...G..A....................G..................G.C...  720
3  .....................................................  569

1  TCATACCCGACAGGGAAGTCCTCTACCGGGAGTTCGATGAGATGGAAGAGTGCTCTCAGC  780
2  .........T.................A.................................  780
3  ............................................................  569

1  ACTTGCCATATACATCGAGCAAGGGATGATGCTCGCCGAGCAGTTCAAGCAGAAGGCCCTCG  840
2  ....A..G......................................................  840
3  ..............................................................  569

1  GCCTCCTGCAAAACACGGTCCCCGCAGGAGGTCATCACCCCTGCTGTCCAGACCAACT  900
2  ..............G..CGC........T.................T...G........  900
3  ..........................................................  569

1  GGCAGAGACTCGAGGCCTTCTGGGCGAAGCATATGTGGAACTT  943
2  ....A..A.............A.....................  943
3  ...........................................  569
```

*FIG. 8C*

```
1   NTCNVQTVDFSLDPTFTIETTTLPQDAVSRTQRRGRTGRGKPGIYRFVAPGERPSGMFDS    60
2   ................I.................L.....V...RR......T....A.    60
3   ................I.................L.....V...RR......T....A.    60

1   SVLCECYDAGCAWYELTPAETTVRLRAYMNTPGLPVCQDHLEFWEGVFTGLTHIDAHFLS   120
2   ...........................S........L......................   120
3   ...........................S........L......................   120

1   QTKQSGENLPYLVAYQATVCARAQAPPPSWDQMWKCLIRLKPTLHGPTPLLYRLGAVQNE   180
2   .....A.D.F..................K...............................  180
3   .....A.D.F..................K...............................  180

1   VTLTMPITKYIMTCMSADLEVVTSTWVLVGGVLAALAAYCLSTGCVVIVGRVILSGKPAI   240
2   I......V..................................V.................  240
3   I......V.                                                     189

1   IPDREVLYREFDEMEECSQHLPYIEQGMMLAEQFKQKALGLLQTRSRQAEVITPAVQTNW   300
2   ................................A......A......A......E....   300
3                                                                 189

1   QRLEAFWAKHMWN                                                 313
2   ..K..T.......                                                 313
3                                                                 189
```

FIG. 9

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 256 base pairs
      (B) TYPE: nucleic acid
      (C) STRANDEDNESS: single
      (D) TOPOLOGY: linear (ii) MOLECULE TYPE: Other
      (A) DESCRIPTION: cDNA to genomic RNA (xi) SEQUENCE DESCRIPTION: SEQ ID NO:1:

```
CCATGGCGTT AGTATGAGTG TCGTACAGCC TCCAGGACCC CCCCTCCCGG GAGAGCCATA      60

GTGGTCTGCG GAGCCGGTGA GTACACCGGA ATTGCCAGGA CGACCGGGTC CTTTCTTGGA     120

TCAACCCGCT CAATGCCTGG AGATTTGGGC GTGCCCCCGC AAGACTGCTA GCCGAGTAGT     180

GTTGGGTCGC GAAAGGCCTT GTGGTACTGC CTGATAGGGT GCTTGCGAGT GCCCCGGGAG     240

GTCTCGTAGA CCGTGC                                                    256
```

(2) INFORMATION FOR SEQ ID NO:2:

(i) SEQUENCE CHARACTERISTICS:
    (A) LENGTH: 501 base pairs
    (B) TYPE: nucleic acid
    (C) STRANDEDNESS: single
    (D) TOPOLOGY: linear (ii) MOLECULE TYPE: Other
    (A) DESCRIPTION: cDNA to genomic RNA (xi) SEQUENCE DESCRIPTION: SEQ ID NO:2:

```
TTCTGGAAGA CGGCGTGAAC TATGCAACAG GGAACCTTCC TGGTTGCTCT TTCTCTATCC      60

TCCTCCTGGC CCTGCTCTCT TGCCTGACTG TGCCCGCGTC AGCCTACCAA GTACGCAATT     120

CTCGCGGCCT TTACCATGTC ACCAATGATT GCCCTAACTC GAGTATTGTG TACGAGACGG     180

CCGATAGCAT TCTACACTCT CCGGGGTGTG TCCCTTGCGT TCGCGAGGGT AACACCTCGA     240

AATGTTGGGT GGCGGTGGCC CCTACAGTCG CCACCAGAGA CGGCAGACTC CCCACAACGC     300

AGCTTCGACG TCATATCGAT CTGCTCGTCG GGAGCGCCAC CCTCTGCTCG GCCCTCTATG     360

TGGGGGACTT GTGCGGGTCC GTCTTCCTCG TCGGTCAATT GTTCACCTTC TCCCCCAGGC     420

GCCACTGGAC AACGCAAGAC TGCAACTGTT CCATCTACCC CGGCCACGTA ACGGGTCACC     480

GCATGGCATG GGATATGATG A                                               501
```

(2) INFORMATION FOR SEQ ID NO:3:

(i) SEQUENCE CHARACTERISTICS:
    (A) LENGTH: 166 amino acids
    (B) TYPE: amino acid
    (D) TOPOLOGY: linear (ii) MOLECULE TYPE: peptide (xi) SEQUENCE DESCRIPTION: SEQ ID NO:3:

```
Leu Glu Asp Gly Val Asn Tyr Ala Thr Gly Asn Leu Pro Gly Cys Ser
1               5                   10                  15

Phe Ser Ile Leu Leu Ala Leu Leu Ser Cys Leu Thr Val Pro Ala
            20                  25                  30

Ser Ala Tyr Gln Val Arg Asn Ser Arg Gly Leu Tyr His Val Thr Asn
            35                  40                  45

Asp Cys Pro Asn Ser Ser Ile Val Tyr Glu Thr Ala Asp Ser Ile Leu
50                  55                  60

His Ser Pro Gly Cys Val Pro Cys Val Arg Glu Gly Asn Thr Ser Lys
65                  70                  75                  80

Cys Trp Val Ala Val Ala Pro Thr Val Ala Thr Arg Asp Gly Arg Leu
            85                  90                  95

Pro Thr Thr Gln Leu Arg Arg His Ile Asp Leu Leu Val Gly Ser Ala
            100                 105                 110

Thr Leu Cys Ser Ala Leu Tyr Val Gly Asp Leu Cys Gly Ser Val Phe
            115                 120                 125

Leu Val Gly Gln Leu Phe Thr Phe Ser Pro Arg Arg His Trp Thr Thr
130                 135                 140

Gln Asp Cys Asn Cys Ser Ile Tyr Pro Gly His Val Thr Gly His Arg
145                 150                 155                 160

Met Ala Trp Asp Met Met
                165
```

(2) INFORMATION FOR SEQ ID NO:4:

(i) SEQUENCE CHARACTERISTICS:
    (A) LENGTH: 1210 base pairs

```
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:4:

AATGGCTCAA CTGCTCAGGG TCCCGCAAGC CATCTTGGAC ATGATCGCTG GTGCCCACTG    60

GGGAGTCCTA GCGGGCATAG CGTATTTCTC CATGGTGGGG AACTGGGCGA AGGTCCTGCT   120

AGTGCTGTTG CTGTTCGCCG GCGTCGATGC GGAAACCTAC ACCACCGGGG GGAGTACTGC   180

CAGGACCACG CAAGGACTCG TCAGCCTTTT CAGTCGAGGC GCCAAGCAGG ACATCCAGCT   240

GATCAACACC AACGGCAGCT GGCACATTAA TCGCACAGCT TTGAACTGTA ATGAGAGCCT   300

CGACACCGGC TGGGTAGCGG GGCTCTTCTA TTACCACAAA TTCAACTCTT CAGGCTGCCC   360

CGAGAGGATG GCCAGCTGCA GACCCCTTGC CGATTTCGAC CAGGGCTGGG GCCCTATCAG   420

TTATGCCAAC GGAACCGGCC CTGAACACCG CCCCTACTGC TGGCACTACC CCCCAAAGCC   480

TTGTGGTATC GTGCCAGCAC AGACCGTATG TGGCCCAGTG TATTGCTTCA CTCCTAGCCC   540

CGTGGTGGTG GGGACGACCA ATAAGTTGGG CGCACCCACT TACAACTGGG GTTGTAATGA   600

TACGGACGTC TTCGTCCTTA ATAACACCAG GCCACCGCTG GGCAATTGGT TCGGCTGCAC   660

CTGGGTGAAC TCATCTGGAT TTACTAAAGT GTGCGGAGCG CCTCCCTGTG TCATCGGAGG   720

AGCGGGCAAT AACACCTTGT ACTGCCCCAC TGACTGTTTC CGCAAGCATC CGGAAGCTAC   780

ATACTCCCGA TGTGGCTCCG GTCCTTGGAT CACGCCCAGG TGCCTGGTTG GCTATCCTTA   840

TAGGCTCTGG CATTATCCCT GTACTGTCAA CTACACCCTG TTCAAGGTCA GGATGTACGT   900

GGGAGGGGTC GAGCACAGGC TGCAAGTCGC TTGCAACTGG ACGCGGGGCG AGCGTTGTAA   960

TCTGGACGAC AGGGACAGGT CCGAGCTCAG TCCGCTGCTG CTGTCTACCA CACAGTGGCA  1020

GGTCCTCCCG TGTTCCTTTA CGACCTTGCC AGCCTTGACT ACCGGCCTCA TCCACCTCCA  1080

CCAGAACATC GTGGACGTGC AATATTTGTA CGGGGTGGGG TCAAGCATTG TGTCCTGGGC  1140

CATCAAGTGG GAGTACGTCA TTCTCCTGTT TCTCCTGCTT GCAGACGCGC GCGTCTGCTC  1200

CTGCTTGTGG                                                        1210

(2) INFORMATION FOR SEQ ID NO:5:

(i) SEQUENCE CHARACTERISTICS:
        (A) LENGTH: 403 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Met Ala Gln Leu Leu Arg Val Pro Gln Ala Ile Leu Asp Met Ile Ala
1               5                  10                  15

Gly Ala His Trp Gly Val Leu Ala Gly Ile Ala Tyr Phe Ser Met Val
            20                  25                  30

Gly Asn Trp Ala Lys Val Leu Val Leu Leu Phe Ala Gly Val
        35                  40                  45

Asp Ala Glu Thr Tyr Thr Thr Gly Gly Ser Thr Ala Arg Thr Thr Gln
    50                  55                  60

Gly Leu Val Ser Leu Phe Ser Arg Gly Ala Lys Gln Asp Ile Gln Leu
65                  70                  75                  80
```

```
Ile Asn Thr Asn Gly Ser Trp His Ile Asn Arg Thr Ala Leu Asn Cys
                85                  90                  95
Asn Glu Ser Leu Asp Thr Gly Trp Val Ala Gly Leu Phe Tyr Tyr His
            100                 105                 110
Lys Phe Asn Ser Ser Gly Cys Pro Glu Arg Met Ala Ser Cys Arg Pro
        115                 120                 125
Leu Ala Asp Phe Asp Gln Gly Trp Gly Pro Ile Ser Tyr Ala Asn Gly
    130                 135                 140
Thr Gly Pro Glu His Arg Pro Tyr Cys Trp His Tyr Pro Pro Lys Pro
145                 150                 155                 160
Cys Gly Ile Val Pro Ala Gln Thr Val Cys Gly Pro Val Tyr Cys Phe
                165                 170                 175
Thr Pro Ser Pro Val Val Val Gly Thr Thr Asn Lys Leu Gly Ala Pro
            180                 185                 190
Thr Tyr Asn Trp Gly Cys Asn Asp Thr Asp Val Phe Val Leu Asn Asn
        195                 200                 205
Thr Arg Pro Pro Leu Gly Asn Trp Phe Gly Cys Thr Trp Val Asn Ser
    210                 215                 220
Ser Gly Phe Thr Lys Val Cys Gly Ala Pro Pro Cys Val Ile Gly Gly
225                 230                 235                 240
Ala Gly Asn Asn Thr Leu Tyr Cys Pro Thr Asp Cys Phe Arg Lys His
                245                 250                 255
Pro Glu Ala Thr Tyr Ser Arg Cys Gly Ser Gly Pro Trp Ile Thr Pro
            260                 265                 270
Arg Cys Leu Val Gly Tyr Pro Tyr Arg Leu Trp His Tyr Pro Cys Thr
        275                 280                 285
Val Asn Tyr Thr Leu Phe Lys Val Arg Met Tyr Val Gly Gly Val Glu
    290                 295                 300
His Arg Leu Gln Val Ala Cys Asn Trp Thr Arg Gly Glu Arg Cys Asn
305                 310                 315                 320
Leu Asp Asp Arg Asp Arg Ser Glu Leu Ser Pro Leu Leu Leu Ser Thr
                325                 330                 335
Thr Gln Trp Gln Val Leu Pro Cys Ser Phe Thr Thr Leu Pro Ala Leu
            340                 345                 350
Thr Thr Gly Leu Ile His Leu His Gln Asn Ile Val Asp Val Gln Tyr
        355                 360                 365
Leu Tyr Gly Val Gly Ser Ser Ile Val Ser Trp Ala Ile Lys Trp Glu
    370                 375                 380
Tyr Val Ile Leu Leu Phe Leu Leu Leu Ala Asp Ala Arg Val Cys Ser
385                 390                 395                 400
Cys Leu Trp (2) INFORMATION FOR SEQ ID NO:6:

(i) SEQUENCE CHARACTERISTICS:
        (A) LENGTH: 943 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:6:

ACAATACGTG TGTCACCCAG ACAGTCGACT TCAGCCTTGA CCCTACCTTC ACCATTGAAA      60

CAACAACGCT TCCCCAGGAT GCTGTCTCCC GCACTCAACG TCGGGGCAGG ACTGGCAGGG     120
```

-continued

```
GGAAGCCAGG CATTTACAGA TTTGTGGCAC CTGGAGAGCG CCCCTCCGGC ATGTTCGACT    180

CGTCCGTCCT CTGCGAGTGC TATGACGCAG GCTGTGCTTG GTATGAGCTC ACGCCCGCCG    240

AGACCACAGT CAGGCTACGA GCATACATGA ACACCCCGGG ACTTCCCGTG TGCCAAGACC    300

ATCTTGAGTT TTGGGAGGGC GTCTTCACGG GTCTCACCCA TATAGACGCC CACTTCCTAT    360

CCCAGACAAA GCAGAGTGGG GAAAACCTTC CTTACCTGGT AGCGTACCAA GCCACCGTGT    420

GCGCTAGGGC CCAAGCCCCT CCCCGTCGT GGGACCAGAT GTGGAAGTGC TTGATTCGTC     480

TCAAGCCCAC CCTCCATGGG CCAACACCCC TGCTATACCG ACTGGGCGCT GTTCAGAATG    540

AAGTCACCCT GACGCACCCA ATCACCAAAT ATATCATGAC ATGCATGTCG GCTGACCTGG    600

AGGTCGTCAC GAGTACCTGG GTGCTCGTGG GCGGCGTTCT GGCTGCTTTG GCCGCGTATT    660

GCCTATCCAC AGGCTGCGTG GTCATAGTAG GCAGGGTCAT TTTGTCCGGG AAGCCGGCAA    720

TCATACCCGA CAGGGAAGTC CTCTACCGGG AGTTCGATGA GATGGAAGAG TGCTCTCAGC    780

ACTTGCCATA CATCGAGCAA GGGATGATGC TCGCCGAGCA GTTCAAGCAG AAGGCCCTCG    840

GCCTCCTGCA AACACGGTCC CGCCAGGCAG AGGTCATCAC CCCTGCTGTC CAGACCAACT    900

GGCAGAGACT CGAGGCCTTC TGGGCGAAGC ATATGTGGAA CTT                     943
```

(2) INFORMATION FOR SEQ ID NO:7:

(i) SEQUENCE CHARACTERISTICS:
        (A) LENGTH: 313 amino acids
        (B) TYPE: amino acid
        (D) TOPOLOGY: linear (ii) MOLECULE TYPE: peptide (xi) SEQUENCE DESCRIPTION: SEQ ID NO:7:

```
Asn Thr Cys Val Thr Gln Thr Val Asp Phe Ser Leu Asp Pro Thr Phe
 1               5                  10                  15

Thr Ile Glu Thr Thr Leu Pro Gln Asp Ala Val Ser Arg Thr Gln
             20                  25                  30

Arg Arg Gly Arg Thr Gly Arg Gly Lys Pro Gly Ile Tyr Arg Phe Val
             35                  40                  45

Ala Pro Gly Glu Arg Pro Ser Gly Met Phe Asp Ser Ser Val Leu Cys
 50                  55                  60

Glu Cys Tyr Asp Ala Gly Cys Ala Trp Tyr Glu Leu Thr Pro Ala Glu
 65                  70                  75                  80

Thr Thr Val Arg Leu Arg Ala Tyr Met Asn Thr Pro Gly Leu Pro Val
             85                  90                  95

Cys Gln Asp His Leu Glu Phe Trp Glu Gly Val Phe Thr Gly Leu Thr
                100                 105                 110

His Ile Asp Ala His Phe Leu Ser Gln Thr Lys Gln Ser Gly Glu Asn
             115                 120                 125

Leu Pro Tyr Leu Val Ala Tyr Gln Ala Thr Val Cys Ala Arg Ala Gln
 130                 135                 140

Ala Pro Pro Pro Ser Trp Asp Gln Met Trp Lys Cys Leu Ile Arg Leu
145                 150                 155                 160

Lys Pro Thr Leu His Gly Pro Thr Pro Leu Leu Tyr Arg Leu Gly Ala
                165                 170                 175

Val Gln Asn Glu Val Thr Leu Thr His Pro Ile Thr Lys Tyr Ile Met
             180                 185                 190

Thr Cys Met Ser Ala Asp Leu Glu Val Val Thr Ser Thr Trp Val Leu
             195                 200                 205
```

```
Val Gly Gly Val Leu Ala Ala Leu Ala Ala Tyr Cys Leu Ser Thr Gly
    210                 215                 220
Cys Val Val Ile Val Gly Arg Val Ile Leu Ser Gly Lys Pro Ala Ile
225                 230                 235                 240
Ile Pro Asp Arg Glu Val Leu Tyr Arg Glu Phe Asp Glu Met Glu Glu
                245                 250                 255
Cys Ser Gln His Leu Pro Tyr Ile Glu Gln Gly Met Met Leu Ala Glu
                260                 265                 270
Gln Phe Lys Gln Lys Ala Leu Gly Leu Leu Gln Thr Arg Ser Arg Gln
            275                 280                 285
Ala Glu Val Ile Thr Pro Ala Val Gln Thr Asn Trp Gln Arg Leu Glu
    290                 295                 300
Ala Phe Trp Ala Lys His Met Trp Asn
305                 310
```

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:8:

ACAATACGTG TGTCACC                                     17

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:9:

AAGTTCCACA TATGCTTCGC                                20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:10:

TCCGTTGGCA TAACTGATAG                                20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
            (A) DESCRIPTION: DNA primer (xi) SEQUENCE DESCRIPTION: SEQ ID NO:11:

CTATCAGTTA TGCCAACGGA                                                    20

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other
            (A) DESCRIPTION: DNA primer (xi) SEQUENCE DESCRIPTION: SEQ ID NO:12:

GTTGCCCGCC CCTCCGATGT                                                    20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other
            (A) DESCRIPTION: DNA primer (xi) SEQUENCE DESCRIPTION: SEQ ID NO:13:

CCCAGCCCCG TGGTGGTGGG                                                    20

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other
            (A) DESCRIPTION: DNA primer (xi) SEQUENCE DESCRIPTION: SEQ ID NO:14:

CCACAAGCAG GAGCAGACGC                                                    20

(2) INFORMATION FOR SEQ ID NO:15:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Other
            (A) DESCRIPTION: DNA primer (xi) SEQUENCE DESCRIPTION: SEQ ID NO:15:

CCATGGCGTT AGTATGAGT                                                     19

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Other
            (A) DESCRIPTION: DNA primer (xi) SEQUENCE DESCRIPTION: SEQ ID NO:16:

GCAGGTCTAC GAGACCTC                                                          18

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other
            (A) DESCRIPTION: DNA primer (xi) SEQUENCE DESCRIPTION: SEQ ID NO:17:

TTCTGGAAGA CGGCGTGAAC                                                        20

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other
            (A) DESCRIPTION: DNA primer (xi) SEQUENCE DESCRIPTION: SEQ ID NO:18:

TCATCATATC CCATGCCATG                                                        20

(2) INFORMATION FOR SEQ ID NO:19:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: Other
            (A) DESCRIPTION: DNA probe (xi) SEQUENCE DESCRIPTION: SEQ ID NO:19:

CCTTCACCAT TGAGACAATC ACGCTCCCCC AGGATGCTGT                                   40

(2) INFORMATION FOR SEQ ID NO:20:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: Other
            (A) DESCRIPTION: DNA probe (xi) SEQUENCE DESCRIPTION: SEQ ID NO:20:

CTGTCCTGAG AGGCTAGCCA GCTGCCGACC CCTTACCGAT                                   40

(2) INFORMATION FOR SEQ ID NO:21:

(i) SEQUENCE CHARACTERISTICS:
            (A) LENGTH: 40 base pairs
            (B) TYPE: nucleic acid
            (C) STRANDEDNESS: single (D) TOPOLOGY: linear (ii) MOLECULE TYPE: Other
          (A) DESCRIPTION: DNA probe (xi) SEQUENCE DESCRIPTION: SEQ ID NO:21:

AGGTCGGGCG CGCCCACCTA CAGCTGGGGT GAAAATGATA                    40

(2) INFORMATION FOR SEQ ID NO:22:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: Other
          (A) DESCRIPTION: DNA probe (xi) SEQUENCE DESCRIPTION: SEQ ID NO:22:

GTGCAGCCTC CAGGACCCCC                                         20

(2) INFORMATION FOR SEQ ID NO:23:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: Other
          (A) DESCRIPTION: DNA probe (xi) SEQUENCE DESCRIPTION: SEQ ID NO:23:

CTCGTACACA ATACTCGAGT                                         20

(2) INFORMATION FOR SEQ ID NO:24:

(i) SEQUENCE CHARACTERISTICS:
          (A) LENGTH: 256 base pairs
          (B) TYPE: nucleic acid
          (C) STRANDEDNESS: single
          (D) TOPOLOGY: linear (ii) MOLECULE TYPE: Other
          (A) DESCRIPTION: cDNA to genomic RNA (xi) SEQUENCE DESCRIPTION: SEQ ID NO:24:

CCATGGCGTT AGTATGAGTG TCGTGCAGCC TCCAGGACCC CCCTCCCGG GAGAGCCATA    60

GTGGTCTGCG GAACCGGTGA GTACACCGGA ATTGCCAGGA CGACCGGGTC CTTTCTTGGA  120

TAAACCCGCT CAATGCCTGG AGATTTGGGC GCGCCCCCGC GAGACTGCTA GCCGAGTAGT  180

GTTGGGTCGC GAAAGGCCTT GTGGTACTGC CTGATAGGGT GCTTGCGAGT GCCCCGGGAG  240

GTCTCGTAGA CCGTGC                                                 256

(2) INFORMATION FOR SEQ ID NO:25:

(i) SEQUENCE CHARACTERISTICS:
          (A) LENGTH: 256 base pairs
          (B) TYPE: nucleic acid
          (C) STRANDEDNESS: single
          (D) TOPOLOGY: linear (ii) MOLECULE TYPE: Other
          (A) DESCRIPTION: cDNA to genomic RNA (xi) SEQUENCE DESCRIPTION: SEQ ID NO:25:

```
CCATGGCGTT AGTATGAGTG TCGTGCAGCC TCCAGGACCC CCCCTCCCGG GAGAGCCATA      60

GTGGTCTGCG GAGCCGGTGA GTACACCGGA ATTGCCAGGA CGACCGGGTC CTTTCTTGGA     120

TAAACCCGCT CAATGCCTGG AGATTTGGGC GCGCCCCCGC AAGACTGCTA GCCGAGTAGT     180

GTTGGGTCGC GAAAGGCCTT GTGGTACTGC CTGATAGGGT GCTTGCGAGT GCCCCGGGAG     240

GTCTCGTAGA CCGTGC                                                    256
```

(2) INFORMATION FOR SEQ ID NO:26:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:26:

```
CCATGGCGTT AGTATGAGTG TCGTGCAGCC TCCAGGACCC CCCCTCCCGG GAGAGCCATA      60

GTGGTCTGCG GAACCGGTGA GTACACCGGA ATTGCCAGGA CGACCGGGTC CTTTCTTGGA     120

TAAACCCGCT CAATGCCTGG AGATTTGGGC GCGCCCCCGC GAGACTGCTA GCCGAGTAGT     180

GTTGGGTCGC GAAAGGCCTT GTGGTACTGC CTGATAGGGT GCTTGCGAGT GCCCCGGGAG     240

GTCTCGTAGA CCGTGC                                                    256
```

(2) INFORMATION FOR SEQ ID NO:27:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:27:

```
TTCTGGAAGA CGGCGTGAAC TATGCAACAG GGAACCTTCC TGGTTGCTCT TTCTCTATCT      60

TCCTTCTGGC CCTGCTCTCT TGCTTGACTG TGCCCGCTTC GGCCTACCAA GTGCGCAATT     120

CCACGGGGCT TTACCACGTC ACCAATGATT GCCCTAACTC GAGTATTGTG TACGAGGCGG     180

CCGATGCCAT CCTGCACACT CCGGGGTGCG TCCCTTGCGT TCGTGAGGGC AACGCCTCGA     240

GGTGTTGGGT GGCGATGACC CCTACGGTGG CCACCAGGGA TGGAAGACTC CCCGCGACGC     300

AGCTTCGACG TCACATCGAT CTGCTTGTCG GGAGCGCCAC CCTCTGTTCG GCCCTCTACG     360

TGGGGGACCT ATGCGGGTCT GTCTTTCTTG TCGGCCAATT GTTCACCTTC TCTCCCAGGC     420

GCCACTGGAC GACGCAAGGT TGCAATTGCT CTATCTATCC CGGCCATATA ACGGGTCACC     480

GCATGGCATG GGATATGATG A                                              501
```

(2) INFORMATION FOR SEQ ID NO:28:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:28:

```
TTCTGGAGGA CGGCGTGAAC TATGCAACAG GGAATTTGCC CGGTTGCTCT TTCTCTATCT      60

TCCTCTTGGC TCTGCTGTCC TGTTTGACCA TCCCAGCTTC CGCTTATGAA GTGCGCAACG     120

TGTCCGGGAT ATACCATGTC ACAAACGACT GCTCCAACTC AAGCATTGTG TATGAGGCGG     180

CGGACGTGAT CATGCATGCC CCCGGGTGCG TGCCCTGCGT TCGGGAGAAC AATTCCTCCC     240

GTTGCTGGGT AGCGCTCACT CCCACGCTCG CGGCCAGGAA TGCCAGCGTC CCCACTACGA     300

CATTACGACG CCACGTCGAC TTGCTCGTTG GGACGGCTGC TTTCTGCTCC GCTATGTACG     360

TGGGGGATCT CTGCGGATCT GTTTTCCTCA TCTCCCAGCT GTTCACCTTC TCGCCTCGCC     420

GGCATGAGAC AGTACAGGAC TGCAACTGCT CAATCTATCC CGGCCACGTA TCAGGCCATC     480

GCATGGCTTG GGATATGATG A                                               501

(2) INFORMATION FOR SEQ ID NO:29:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:29:

TTCTGGAAGA CGGCGTGAAC TATGCAACAG GGAACCTTCC TGGTTGCTCT TTCTCTATCT      60

TCCTTCTGGC CCTGCTCTCT TGCCTGACTG TGCCCGCTTC AGCCTACCAA GTGCGCAACT     120

CCACAGGGCT TTATCATGTC ACCAATGATT GCCCTAACTC GAGTATTGTG TACGAGGCGC     180

ACGATGCCAT CCTGCATACT CCGGGGTGTG TCCCTTGCGT TCGCGAGGGC AACGTCTCGA     240

GGTGTTGGGT GGCGATGACC CCCACGGTAG CCACCAGGGA CGGAAGACTC CCCGCGACGC     300

AGCTTCGACG TCACATCGAT CTGCTTGTCG GGAGCGCCAC CCTCTGTTCG GCCCTCTACG     360

TGGGGGATCT GTGCGGGTCC GTCTTCCTTA TTGGTCAACT GTTTACCTTC TCTCCCAGGC     420

GCCACTGGAC AACGCAAGGC TGCAATTGTT CTATCTACCC CGGCCATATA ACGGGTCATC     480

GCATGGCATG GGATATGATG A                                               501

(2) INFORMATION FOR SEQ ID NO:30:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:30:

TTCTGGAGGA CGGCGTGAAC TATGCAACAG GGAACTTGCC CGGTTGCTCT TTCTCTATCT      60

TCCTCTTGGC TTTGCTGTCC TGTTTGACCA TCCCAGCTTC CGCTTATGAA GTGCGCAACG     120

TGTCCGGGAT ATACCATGTC ACGAACGACT GCTCCAACTC AAGCATTGTG TATGAGGCAG     180

CGGACATGAT CATGCATACT CCCGGGTGCG TGCCCTGCGT TCGGGAGGAC AACAGCTCCC     240

GTTGCTGGGT AGCGCTCACT CCCACGCTCG CGGCCAGGAA TGCCAGCGTC CCCACTACGA     300

CAATACGACG CCACGTCGAC TTGCTCGTTG GGGCGGCTGC TTTCTGCTCC GCTATGTACG     360

TGGGGGATCT CTGCGGATCT GTTTTCCTCG TCTCCCAGCT GTTCACCTTC TCGCCTCGCC     420
```

```
GGCATGAGAC AGTGCAGGAC TGCAACTGCT CAATCTATCC CGGCCATTTA TCAGGTCACC    480

GCATGGCTTG GGATATGATG A                                              501
```

(2) INFORMATION FOR SEQ ID NO:31:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:31:

```
Leu Glu Asp Gly Val Asn Tyr Ala Thr Gly Asn Leu Pro Gly Cys Ser
1               5                   10                  15

Phe Ser Ile Phe Leu Leu Ala Leu Leu Ser Cys Leu Thr Val Pro Ala
            20                  25                  30

Ser Ala Tyr Gln Val Arg Asn Ser Thr Gly Leu Tyr His Val Thr Asn
        35                  40                  45

Asp Cys Pro Asn Ser Ser Ile Val Tyr Glu Ala Ala Asp Ala Ile Leu
    50                  55                  60

His Thr Pro Gly Cys Val Pro Cys Val Arg Glu Gly Asn Ala Ser Arg
65                  70                  75                  80

Cys Trp Val Ala Met Thr Pro Thr Val Ala Thr Arg Asp Gly Arg Leu
                85                  90                  95

Pro Ala Thr Gln Leu Arg Arg His Ile Asp Leu Leu Val Gly Ser Ala
                100                 105                 110

Thr Leu Cys Ser Ala Leu Tyr Val Gly Asp Leu Cys Gly Ser Val Phe
            115                 120                 125

Leu Val Gly Gln Leu Phe Thr Phe Ser Pro Arg Arg His Trp Thr Thr
130                 135                 140

Gln Gly Cys Asn Cys Ser Ile Tyr Pro Gly His Ile Thr Gly His Arg
145                 150                 155                 160

Met Ala Trp Asp Met Met
                165
```

(2) INFORMATION FOR SEQ ID NO:32:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:32:

```
Leu Glu Asp Gly Val Asn Tyr Ala Thr Gly Asn Leu Pro Gly Cys Ser
1               5                   10                  15

Phe Ser Ile Phe Leu Leu Ala Leu Leu Ser Cys Leu Thr Ile Pro Ala
            20                  25                  30

Ser Ala Tyr Glu Val Arg Asn Val Ser Gly Ile Tyr His Val Thr Asn
        35                  40                  45

Asp Cys Ser Asn Ser Ser Ile Val Tyr Glu Ala Ala Asp Val Ile Met
    50                  55                  60

His Ala Pro Gly Cys Val Pro Cys Val Arg Glu Asn Asn Ser Ser Arg
65                  70                  75                  80

Cys Trp Val Ala Leu Thr Pro Thr Leu Ala Ala Arg Asn Ala Ser Val
                85                  90                  95
```

```
Pro Thr Thr Thr Leu Arg Arg His Val Asp Leu Leu Val Gly Thr Ala
            100                 105                 110

Ala Phe Cys Ser Ala Met Tyr Val Gly Asp Leu Cys Gly Ser Val Phe
            115                 120                 125

Leu Ile Ser Gln Leu Phe Thr Phe Ser Pro Arg Arg His Glu Thr Val
        130                 135                 140

Gln Asp Cys Asn Cys Ser Ile Tyr Pro Gly His Val Ser Gly His Arg
145                 150                 155                 160

Met Ala Trp Asp Met Met
                165

(2) INFORMATION FOR SEQ ID NO:33:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:33:

Leu Glu Asp Gly Val Asn Tyr Ala Thr Gly Asn Leu Pro Gly Cys Ser
1               5                   10                  15

Phe Ser Ile Phe Leu Leu Ala Leu Leu Ser Cys Leu Thr Val Pro Ala
            20                  25                  30

Ser Ala Tyr Gln Val Arg Asn Ser Thr Gly Leu Tyr His Val Thr Asn
        35                  40                  45

Asp Cys Pro Asn Ser Ser Ile Val Tyr Glu Ala His Asp Ala Ile Leu
    50                  55                  60

His Thr Pro Gly Cys Val Pro Cys Val Arg Glu Gly Asn Val Ser Arg
65                  70                  75                  80

Cys Trp Val Ala Met Thr Pro Thr Val Ala Thr Arg Asp Gly Arg Leu
                85                  90                  95

Pro Ala Thr Gln Leu Arg Arg His Ile Asp Leu Leu Val Gly Ser Ala
            100                 105                 110

Thr Leu Cys Ser Ala Leu Tyr Val Gly Asp Leu Cys Gly Ser Val Phe
            115                 120                 125

Leu Ile Gly Gln Leu Phe Thr Phe Ser Pro Arg Arg His Trp Thr Thr
        130                 135                 140

Gln Gly Cys Asn Cys Ser Ile Tyr Pro Gly His Ile Thr Gly His Arg
145                 150                 155                 160

Met Ala Trp Asp Met Met
                165

(2) INFORMATION FOR SEQ ID NO:34:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:34:

Leu Glu Asp Gly Val Asn Tyr Ala Thr Gly Asn Leu Pro Gly Cys Ser
1               5                   10                  15

Phe Ser Ile Phe Leu Leu Ala Leu Leu Ser Cys Leu Thr Ile Pro Ala
            20                  25                  30

Ser Ala Tyr Glu Val Arg Asn Val Ser Gly Ile Tyr His Val Thr Asn
```

```
                35                  40                  45
Asp Cys Ser Asn Ser Ser Ile Val Tyr Glu Ala Ala Asp Met Ile Met
         50                  55                  60

His Thr Pro Gly Cys Val Pro Cys Val Arg Glu Asp Asn Ser Ser Arg
 65                  70                  75                  80

Cys Trp Val Ala Leu Thr Pro Thr Leu Ala Ala Arg Asn Ala Ser Val
                 85                  90                  95

Pro Thr Thr Thr Ile Arg Arg His Val Asp Leu Leu Val Gly Ala Ala
                100                 105                 110

Ala Phe Cys Ser Ala Met Tyr Val Gly Asp Leu Cys Gly Ser Val Phe
            115                 120                 125

Leu Val Ser Gln Leu Phe Thr Phe Ser Pro Arg Arg His Glu Thr Val
        130                 135                 140

Gln Asp Cys Asn Cys Ser Ile Tyr Pro Gly His Leu Ser Gly His Arg
145                 150                 155                 160

Met Ala Trp Asp Met Met
                165
```

(2) INFORMATION FOR SEQ ID NO:35:

(i) SEQUENCE CHARACTERISTICS:
        (A) LENGTH: 1210 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:35:

```
AATGGCTCAG CTGCTCCGGA TCCCACAAGC CATCTTGGAC ATGATCGCTG GTGCTCACTG     60

GGGAGTCCTG GCGGGCATAG CGTATTTCTC CATGGTGGGG AACTGGGCGA AGGTCCTGGT    120

AGTGCTGCTG CTATTTGCCG GCGTCGACGC GGAAACCCAC GTCACCGGGG AAGTGCCGG     180

CCACACTGTG TCTGGATTTG TTAGCCTCCT CGCACCAGGC GCCAAGCAGA ACGTCCAGCT    240

GATCAACACC AACGGCAGTT GGCACCTCAA TAGCACGGCT CTGAACTGCA ATGATAGCCT    300

TAACACCGGC TGGTTGGCAG GCTTTTCTA TCACCACAAG TTCAACTCTT CAGGCTGTCC     360

TGAGAGGCTA GCCAGCTGCC GACCCCTTAC CGATTTTGAC CAGGGCTGGG GCCCTATCAG    420

TTATGCCAAC GGAAGCGGCC CCGACCAGCG CCCCTACTGC TGGCACTACC CCCAAAAACC    480

TTGCGGTATT GTGCCCGCGA AGAGTGTGTG TGGTCCGGTA TATTGCTTCA CTCCCAGCCC    540

CGTGGTGGTG GGAACGACCG ACAGGTCGGG CGCGCCCACC TACAGCTGGG GTGAAAATGA    600

TACGGACGTC TTCGTCCTTA ACAATACCAG GCCACCGCTG GGCAATTGGT TCGGTTGTAC    660

CTGGATGAAC TCAACTGGAT TCACCAAAGT GTGCGGAGCG CCTCCTTGTG TCATCGGAGG    720

GGCGGGCAAC AACACCCTGC ACTGCCCCAC TGATTGCTTC CGCAAGCATC CGGACGCCAC    780

ATACTCTCGG TGCGGCTCCG GTCCCTGGAT CACACCCAGG TGCCTGGTCG ACTACCCGTA    840

TAGGCTTTGG CATTATCCTT GTACCATCAA CTACACCATA TTTAAAATCA GGATGTACGT    900

GGGAGGGGTC GAACACAGGC TGGAAGCTGC CTGCAACTGG ACGCGGGGCG AACGTTGCGA    960

TCTGGAAGAC AGGGACAGGT CCGAGCTCAG CCCGTTACTG CTGACCACTA CACAGTGGCA   1020

GGTCCTCCCG TGTTCCTTCA CAACCCTACC AGCCTTGTCC ACCGGCCTCA TCCACCTCCA   1080

CCAGAACATT GTGGACGTGC AGTACTTGTA CGGGGTGGGG TCAAGCATCG CGTCCTGGGC   1140

CATTAAGTGG GAGTACGTCG TTCTCCTGTT CCTTCTGCTT GCAGACGCGC GCGTCTGCTC   1200
```

```
CTGCTTGTGG                                                            1210

(2) INFORMATION FOR SEQ ID NO:36:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:36:

AATGGCTCAG CTGCTCCGCA TCCCACAAGC CATCTTGGAT ATGATCGCTG GTGCTCACTG      60

GGGAGTCCTG GCGGGCATAG CGTATTTCTC CATGGTGGGG AACTGGGCGA AGGTCCTGGT    120

AGTGCTGTTG CTGTTTGCCG GCGTCGACGC GGAAACCATC GTCTCCGGGG GACAAGCCGC    180

CCGCGCCATG TCTGGACTTG TTAGTCTCTT CACACCAGGC GCTAAGCAGA ACATCCAGCT    240

GATCAACACC AACGGCAGTT GGCACATCAA TAGCACGGCC TTGAACTGCA ATGAAAGCCT    300

TAACACCGGC TGGTTAGCAG GGCTTATCTA TCAACACAAA TTCAACTCTT CGGGCTGTCC    360

CGAGAGGTTG GCCAGCTGCC GACGCCTTAC CGATTTTGAC CAGGGCTGGG GCCCTATCAG    420

TCATGCCAAC GGAAGCGGCC CCGACCAACG CCCCTATTGT TGGCACTACC CCCCAAAACC    480

TTGCGGTATC GTGCCCGCAA AGAGCGTATG TGGCCCGGTA TATTGCTTCA CTCCCAGCCC    540

C                                                                    541

(2) INFORMATION FOR SEQ ID NO:37:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:37:

GGTGTCGCAG TTGCTCCGGA TCCCACAAGC TGTCGTGGAC ATGGTGGCGG GGGCCCACTG      60

GGGAGTCCTG GCGGGCCTTG CCTACTATTC CATGGTAGGG AACTGGGCTA AGGTCCTGAT    120

TGTGGCGCTA CTCTTCGCCG GCGTTGACGG GGAGACCTAC ACGTCGGGGG GGGCGGCCAG    180

CCACACCACC TCCACGCTCG CGTCCCTCTT CTCACCTGGG GCGTCTCAGA GAATCCAGCT    240

TGTGAATACC AACGGCAGCT GGCACATCAA CAGGACTGCC CTAAACTGCA ATGACTCCCT    300

CCACACTGGG TTCCTTGCCG CGCTGTTCTA CACACACAGG TTCAACTCGT CCGGGTGCCC    360

GGAGCGCATG GCCAGCTGCC GCCCCATTGA CTGGTTCGCC CAGGGATGGG GCCCCATCAC    420

CTATACTGAG CCTGACAGCC CGGATCAGAG GCCTTATTGC TGGCATTACG CGCCTCGACC    480

GTGTGGTATC GTACCCGCGT CGCAGGTGTG TGGTCCAGTG TATTGCTTCA CCCCAAGCCC    540

T                                                                    541

(2) INFORMATION FOR SEQ ID NO:38:

(i) SEQUENCE CHARACTERISTICS:
        (A) LENGTH: 325 base pairs
        (B) TYPE: nucleic acid
        (C) STRANDEDNESS: single
        (D) TOPOLOGY: linear
```

(ii) MOLECULE TYPE: Other
    (A) DESCRIPTION: cDNA to genomic RNA (xi) SEQUENCE DESCRIPTION: SEQ ID NO:38:

```
GGTGTCGCAG TTACTCCGGA TCCCACAAGC TGTCATGGAC ATGGTGGCGG GGGCCCACTG    60

GGGAGTCCTA GCGGGCCTTG CCTACTATTC CATGGTGGGG AACTGGGCTA AGGTTTTGAT   120

TGTGATGCTA CTCTTTGCCG GCGTTGACGG GCATACCCGC GTGACGGGGG GGGTGCAAGG   180

CCACGTCACC TCTACACTCA CGTCCCTCTT TAGACCTGGG GCGTCCCAGA AAATTCAGCT   240

TGTAAACACC AATGGCAGTT GGCATATCAA CAGGACTGCC CTGAACTGCA ATGACTCCCT   300

CCAAACTGGG TTCCTTGCCG CGCTG                                         325
```

(2) INFORMATION FOR SEQ ID NO:39:

(i) SEQUENCE CHARACTERISTICS:
    (A) LENGTH: 403 amino acids
    (B) TYPE: amino acid
    (D) TOPOLOGY: linear (ii) MOLECULE TYPE: peptide (xi) SEQUENCE DESCRIPTION: SEQ ID NO:39:

```
Met Ala Gln Leu Leu Arg Ile Pro Gln Ala Ile Leu Asp Met Ile Ala
1               5                   10                  15

Gly Ala His Trp Gly Val Leu Ala Gly Ile Ala Tyr Phe Ser Met Val
            20                  25                  30

Gly Asn Trp Ala Lys Val Leu Val Leu Leu Leu Phe Ala Gly Val
        35                  40                  45

Asp Ala Glu Thr His Val Thr Gly Gly Ser Ala Gly His Thr Val Ser
    50                  55                  60

Gly Phe Val Ser Leu Leu Ala Pro Gly Ala Lys Gln Asn Val Gln Leu
65                  70                  75                  80

Ile Asn Thr Asn Gly Ser Trp His Leu Asn Ser Thr Ala Leu Asn Cys
                85                  90                  95

Asn Asp Ser Leu Asn Thr Gly Trp Leu Ala Gly Leu Phe Tyr His His
            100                 105                 110

Lys Phe Asn Ser Ser Gly Cys Pro Glu Arg Leu Ala Ser Cys Arg Pro
        115                 120                 125

Leu Thr Asp Phe Asp Gln Gly Trp Gly Pro Ile Ser Tyr Ala Asn Gly
    130                 135                 140

Ser Gly Pro Asp Gln Arg Pro Tyr Cys Trp His Tyr Pro Pro Lys Pro
145                 150                 155                 160

Cys Gly Ile Val Pro Ala Lys Ser Val Cys Gly Pro Val Tyr Cys Phe
                165                 170                 175

Thr Pro Ser Pro Val Val Val Gly Thr Thr Asp Arg Ser Gly Ala Pro
            180                 185                 190

Thr Tyr Ser Trp Gly Glu Asn Asp Thr Asp Val Phe Val Leu Asn Asn
        195                 200                 205

Thr Arg Pro Pro Leu Gly Asn Trp Phe Gly Cys Thr Trp Met Asn Ser
    210                 215                 220

Thr Gly Phe Thr Lys Val Cys Gly Ala Pro Pro Cys Val Ile Gly Gly
225                 230                 235                 240

Ala Gly Asn Asn Thr Leu His Cys Pro Thr Asp Cys Phe Arg Lys His
                245                 250                 255

Pro Asp Ala Thr Tyr Ser Arg Cys Gly Ser Gly Pro Trp Ile Thr Pro
```

```
                    260                 265                 270
Arg Cys Leu Val Asp Tyr Pro Tyr Arg Leu Trp His Tyr Pro Cys Thr
                275                 280                 285
Ile Asn Tyr Thr Ile Phe Lys Ile Arg Met Tyr Val Gly Gly Val Glu
290                 295                 300
His Arg Leu Glu Ala Ala Cys Asn Trp Thr Arg Gly Glu Arg Cys Asp
305                 310                 315                 320
Leu Glu Asp Arg Asp Arg Ser Glu Leu Ser Pro Leu Leu Thr Thr
                325                 330                 335
Thr Gln Trp Gln Val Leu Pro Cys Ser Phe Thr Thr Leu Pro Ala Leu
                340                 345                 350
Ser Thr Gly Leu Ile His Leu His Gln Asn Ile Val Asp Val Gln Tyr
                355                 360                 365
Leu Tyr Gly Val Gly Ser Ser Ile Ala Ser Trp Ala Ile Lys Trp Glu
    370                 375                 380
Tyr Val Val Leu Leu Phe Leu Leu Leu Ala Asp Ala Arg Val Cys Ser
385                 390                 395                 400
Cys Leu Trp (2) INFORMATION FOR SEQ ID NO:40:

(i) SEQUENCE CHARACTERISTICS:
        (A) LENGTH: 180 amino acids
        (B) TYPE: amino acid
        (D) TOPOLOGY: linear (ii) MOLECULE TYPE: peptide (xi) SEQUENCE DESCRIPTION: SEQ ID NO:40:

Met Ala Gln Leu Leu Arg Ile Pro Gln Ala Ile Leu Asp Met Ile Ala
1               5                   10                  15
Gly Ala His Trp Gly Val Leu Ala Gly Ile Ala Tyr Phe Ser Met Val
                20                  25                  30
Gly Asn Trp Ala Lys Val Leu Val Val Leu Leu Phe Ala Gly Val
                35                  40                  45
Asp Ala Glu Thr Ile Val Ser Gly Gly Gln Ala Ala Arg Ala Met Ser
50                  55                  60
Gly Leu Val Ser Leu Phe Thr Pro Gly Ala Lys Gln Asn Ile Gln Leu
65                  70                  75                  80
Ile Asn Thr Asn Gly Ser Trp His Ile Asn Ser Thr Ala Leu Asn Cys
                85                  90                  95
Asn Glu Ser Leu Asn Thr Gly Trp Leu Ala Gly Leu Ile Tyr Gln His
                100                 105                 110
Lys Phe Asn Ser Ser Gly Cys Pro Glu Arg Leu Ala Ser Cys Arg Arg
                115                 120                 125
Leu Thr Asp Phe Asp Gln Gly Trp Gly Pro Ile Ser His Ala Asn Gly
                130                 135                 140
Ser Ala Pro Asp Gln Arg Pro Tyr Cys Trp His Tyr Pro Pro Lys Pro
145                 150                 155                 160
Cys Gly Ile Val Pro Ala Lys Ser Val Cys Gly Pro Val Tyr Cys Phe
                165                 170                 175
Thr Pro Ser Pro
            180

(2) INFORMATION FOR SEQ ID NO:41:
```

(i) SEQUENCE CHARACTERISTICS:
    (A) LENGTH: 180 amino acids
    (B) TYPE: amino acid
    (D) TOPOLOGY: linear (ii) MOLECULE TYPE: peptide (xi) SEQUENCE DESCRIPTION: SEQ ID NO:41:

```
Val Ser Gln Leu Leu Arg Ile Pro Gln Ala Val Val Asp Met Val Ala
1               5                   10                  15

Gly Ala His Trp Gly Val Leu Ala Gly Leu Ala Tyr Tyr Ser Met Val
                20                  25                  30

Gly Asn Trp Ala Lys Val Leu Ile Val Ala Leu Leu Phe Ala Gly Val
                35                  40                  45

Asp Gly Glu Thr Tyr Thr Ser Gly Gly Ala Ala Ser His Thr Thr Ser
        50                  55                  60

Thr Leu Ala Ser Leu Phe Ser Pro Gly Ala Ser Gln Arg Ile Gln Leu
65                  70                  75                  80

Val Asn Thr Asn Gly Ser Trp His Ile Asn Arg Thr Ala Leu Asn Cys
                85                  90                  95

Asn Asp Ser Leu His Thr Gly Phe Leu Ala Ala Leu Phe Tyr Thr His
                100                 105                 110

Arg Phe Asn Ser Ser Gly Cys Pro Glu Arg Met Ala Ser Cys Arg Pro
                115                 120                 125

Ile Asp Trp Phe Ala Gln Gly Trp Gly Pro Ile Thr Tyr Thr Glu Pro
        130                 135                 140

Asp Ser Pro Asp Gln Arg Pro Tyr Cys Trp His Tyr Ala Pro Arg Pro
145                 150                 155                 160

Cys Gly Ile Val Pro Ala Ser Gln Val Cys Gly Pro Val Tyr Cys Phe
                165                 170                 175

Thr Pro Ser Pro
            180
```

(2) INFORMATION FOR SEQ ID NO:42:

(i) SEQUENCE CHARACTERISTICS:
        (A) LENGTH: 108 amino acids
        (B) TYPE: amino acid
        (D) TOPOLOGY: linear (ii) MOLECULE TYPE: peptide (xi) SEQUENCE DESCRIPTION: SEQ ID NO:42:

```
Val Ser Gln Leu Leu Arg Ile Pro Gln Ala Val Met Asp Met Val Ala
1               5                   10                  15

Gly Ala His Trp Gly Val Leu Ala Gly Leu Ala Tyr Tyr Ser Met Val
                20                  25                  30

Gly Asn Trp Ala Lys Val Leu Ile Val Met Leu Leu Phe Ala Gly Val
                35                  40                  45

Asp Gly His Thr Arg Val Thr Gly Gly Val Gln Gly His Val Thr Ser
        50                  55                  60

Thr Leu Thr Ser Leu Phe Arg Pro Gly Ala Ser Gln Lys Ile Gln Leu
65                  70                  75                  80

Val Asn Thr Asn Gly Ser Trp His Ile Asn Arg Thr Ala Leu Asn Cys
                85                  90                  95

Asn Asp Ser Leu Gln Thr Gly Phe Leu Ala Ala Leu
                100                 105
```

(2) INFORMATION FOR SEQ ID NO:43:

(i) SEQUENCE CHARACTERISTICS:
        (A) LENGTH: 943 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:43:

```
ACAATACGTG TGTCACCCAG ACAGTCGATT TCAGCCTTGA CCCTACCTTC ACCATTGAGA    60

CAATCACGCT CCCCCAGGAT GCTGTCTCCC GCACTCAACG TCGGGGCAGG ACTGGCAGGG   120

GGAAGCCAGG CATCTACAGA TTTGTGGCAC CGGGGGAGCG CCCCTCCGGC ATGTTCGACT   180

CGTCCGTCCT CTGTGAGTGC TATGACGCAG GCTGTGCTTG GTATGAGCTC ACGCCCGCCG   240

AGACTACAGT TAGGCTACGA GCGTACATGA ACACCCCGGG GCTTCCCGTG TGCCAGGACC   300

ATCTTGAATT TTGGGAGGGC GTCTTTACAG GCCTCACTCA TATAGATGCC CACTTTCTAT   360

CCCAGACAAA GCAGAGTGGG GAGAACCTTC CTTACCTGGT AGCGTACCAA GCCACCGTGT   420

GCGCTAGGGC TCAAGCCCCT CCCCCATCGT GGGACCAGAT GTGGAAGTGT TTGATTCGCC   480

TCAAGCCCAC CCTCCATGGG CCAACACCCC TGCTATACAG ACTGGGCGCT GTTCAGAATG   540

AAATCACCCT GACGCACCCA GTCACCAAAT ACATCATGAC ATGCATGTCG GCCGACCTGG   600

AGGTCGTCAC GAGCACCTGG GTGCTCGTTG GCGGCGTCCT GGCTGCTTTG GCCGCGTATT   660

GCCTGTCAAC AGGCTGCGTG GTCATAGTGG GCAGGGTCGT CTTGTCCGGG AAGCCGGCAA   720

TCATACCTGA CAGGGAAGTC CTCTACCGAG AGTTCGATGA GATGGAAGAG TGCTCTCAGC   780

ACTTACCGTA CATCGAGCAA GGGATGATGC TCGCCGAGCA GTTCAAGCAG AAGGCCCTCG   840

GCCTCCTGCA GACCGCGTCC CGTCAGGCAG AGGTTATCGC CCCTGCTGTC CAGACCAACT   900

GGCAAAAACT CGAGACCTTC TGGGCGAAGC ATATGTGGAA CTT                    943
```

(2) INFORMATION FOR SEQ ID NO:44:

(i) SEQUENCE CHARACTERISTICS:
        (A) LENGTH: 569 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:44:

```
GTAACACATG TGTCACTCAG ACGGTCGATT TCAGCTTGGA TCCCACTCTC ACCATCGAGA    60

CGACGACCGT GCCCCAAGAT GCGGTTTCGC GCACGCAGCG GCGAGGTAGG ACTGGCAGGG   120

GCAGGAGAGG CATCTATAGG TTTGTGACTC CAGGAGAACG GCCCTCGGCG ATGTTCGATT   180

CTTCGGTCCT ATGTGAGTGT TATGACGCGG GCTGTGCTTG GTATGAGCTC ACGCCCGCTG   240

AGACCTCGGT TAGGTTGCGG GCTTACCTAA ATACACCAGG GTTGCCCGTC TGCCAGGACC   300

ATCTGGAGTT CTGGGAGAGC GTCTTCACAG GCCTCACCCA CATAGACGCC CACTTCTTGT   360

CCCAGACTAA GCAGGCAGGA GACAACTTCC CCTACCTGGT AGCATACCAA GCCACAGTGT   420

GCGCCAGGGC TAAGGCTCCA CCTCCATCGT GGGATCAAAT GTGGAAGTGT CTCATACGGC   480

TAAAGCCTAC GCTGCACGGG CCAACGCCCC TGCTGTATAG GCTAGGAGCC GTCCAGAATG   540

AGGTCACCCT CACACACCCT ATAACCAAA                                    569
```

(2) INFORMATION FOR SEQ ID NO:45:

(i) SEQUENCE CHARACTERISTICS:
        (A) LENGTH: 313 amino acids
        (B) TYPE: amino acid
        (D) TOPOLOGY: linear (ii) MOLECULE TYPE: peptide (xi) SEQUENCE DESCRIPTION: SEQ ID NO:45:

```
Asn Thr Cys Val Thr Gln Thr Val Asp Phe Ser Leu Asp Pro Thr Phe
 1               5                  10                  15

Thr Ile Glu Thr Ile Thr Leu Pro Gln Asp Ala Val Ser Arg Thr Gln
             20                  25                  30

Arg Arg Gly Arg Thr Gly Arg Gly Lys Pro Gly Ile Tyr Arg Phe Val
         35                  40                  45

Ala Pro Gly Glu Arg Pro Ser Gly Met Phe Asp Ser Ser Val Leu Cys
 50                  55                  60

Glu Cys Tyr Asp Ala Gly Cys Ala Trp Tyr Glu Leu Thr Pro Ala Glu
65                  70                  75                  80

Thr Thr Val Arg Leu Arg Ala Tyr Met Asn Thr Pro Gly Leu Pro Val
             85                  90                  95

Cys Gln Asp His Leu Glu Phe Trp Glu Gly Val Phe Thr Gly Leu Thr
         100                 105                 110

His Ile Asp Ala His Phe Leu Ser Gln Thr Lys Gln Ser Gly Glu Asn
     115                 120                 125

Leu Pro Tyr Leu Val Ala Tyr Gln Ala Thr Val Cys Ala Arg Ala Gln
130                 135                 140

Ala Pro Pro Pro Ser Trp Asp Gln Met Trp Lys Cys Leu Ile Arg Leu
145                 150                 155                 160

Lys Pro Thr Leu His Gly Pro Thr Pro Leu Leu Tyr Arg Leu Gly Ala
             165                 170                 175

Val Gln Asn Glu Ile Thr Leu Thr His Pro Val Thr Lys Tyr Ile Met
         180                 185                 190

Thr Cys Met Ser Ala Asp Leu Glu Val Val Thr Ser Thr Trp Val Leu
     195                 200                 205

Val Gly Gly Val Leu Ala Ala Leu Ala Ala Tyr Cys Leu Ser Thr Gly
210                 215                 220

Cys Val Val Ile Val Gly Arg Val Val Leu Ser Gly Lys Pro Ala Ile
225                 230                 235                 240

Ile Pro Asp Arg Glu Val Leu Tyr Arg Glu Phe Asp Glu Met Glu Glu
             245                 250                 255

Cys Ser Gln His Leu Pro Tyr Ile Glu Gln Gly Met Met Leu Ala Glu
         260                 265                 270

Gln Phe Lys Gln Lys Ala Leu Gly Leu Leu Gln Thr Ala Ser Arg Gln
     275                 280                 285

Ala Glu Val Ile Ala Pro Ala Val Glu Thr Asn Trp Gln Lys Leu Glu
290                 295                 300

Thr Phe Trp Ala Lys His Met Trp Asn
305                 310
```

(2) INFORMATION FOR SEQ ID NO:46:

(i) SEQUENCE CHARACTERISTICS:
        (A) LENGTH: 189 amino acids
        (B) TYPE: amino acid
        (D) TOPOLOGY: linear (ii) MOLECULE TYPE: peptide (xi) SEQUENCE DESCRIPTION: SEQ ID NO:46:

```
Asn Thr Cys Val Thr Gln Thr Val Asp Phe Ser Leu Asp Pro Thr Leu
 1               5                  10                  15

Thr Ile Glu Thr Thr Thr Val Pro Gln Asp Ala Val Ser Arg Thr Gln
            20                  25                  30

Arg Arg Gly Arg Thr Gly Arg Gly Arg Arg Gly Ile Tyr Arg Phe Val
        35                  40                  45

Thr Pro Gly Glu Arg Pro Ser Ala Met Phe Asp Ser Ser Val Leu Cys
    50                  55                  60

Glu Cys Tyr Asp Ala Gly Cys Ala Trp Tyr Glu Leu Thr Pro Ala Glu
65                  70                  75                  80

Thr Ser Val Arg Leu Arg Ala Tyr Leu Asn Thr Pro Gly Leu Pro Val
                85                  90                  95

Cys Gln Asp His Leu Glu Phe Trp Glu Ser Val Phe Thr Gly Leu Thr
                100                 105                 110

His Ile Asp Ala His Phe Leu Ser Gln Thr Lys Gln Ala Gly Asp Asn
            115                 120                 125

Phe Pro Tyr Leu Val Ala Tyr Gln Ala Thr Val Cys Ala Arg Ala Lys
    130                 135                 140

Ala Pro Pro Pro Ser Trp Asp Gln Met Trp Lys Cys Leu Ile Arg Leu
145                 150                 155                 160

Lys Pro Thr Leu His Gly Pro Thr Pro Leu Leu Tyr Arg Leu Gly Ala
                165                 170                 175

Val Gln Asn Glu Val Thr Leu Thr His Pro Ile Thr Lys
            180                 185
```

NUCLEOTIDE AND PEPTIDE SEQUENCES OF AN ISOLATE OF THE HEPATITIS C VIRUS, DIAGNOSTIC AND THERAPEUTIC APPLICATIONS THEREOF

This application is a continuation application under 37 C.F.R. §1.53(b) of application Ser. No. 07/965,285, filed Mar. 18, 1993, now U.S. Pat. No. 5,879,904 which claims the benefit of PCT/FR92/00501, filed Jun. 4, 1992, and French application Serial No. FR 91 06 882, filed Jun. 6, 1991.

The present invention relates to nucleotide and peptide sequences of a European, more particularly French, strain of the hepatitis C virus, as well as to the diagnostic and therapeutic applications of these sequences.

The hepatitis C virus is a major causative agent of infections by viruses previously called "Non-A Non-B" viruses. Infections by the C virus in fact now represent the most frequent forms of acute hepatitides and chronic Non-A Non-B hepatitides (Alter et al. (1), Choo et al., (3); Hopf et al., (5); Kuo et al., (8); Miyamura et al., (11). Furthermore, there is a relationship (the significance of which is still poorly understood) between the presence of anti-HCV antibodies and the development of primary liver cancers. It has also been shown that the hepatitis C virus is involved in both chronic or acute Non-A Non-B hepatitides linked to transfusions of blood products or of sporadic origin.

The genome of the hepatitis C virus has been cloned and the nucleotide sequence of an American isolate has been described in EP-A-0 318 216, EP-A-0 363 025, EP-A-0 388 232 and WO-A-90/14436. Moreover, data is currently available on the nucleotide sequences of several Japanese isolates relating both to the structural region and the nonstructural region of the virus (Okamoto et al., (12), Enomoto et al., (4), Kato et al., (6); Takeuchi et al., (15 and 16)). The virus exhibits some similarities with the group comprising Flavi- and Pestiviruses; however, it appears to form a distinct class, different from viruses known up until now (Miller and Purcell, (10)).

In spite of the breakthrough which the cloning of HCV represented, several problems persist:
- a substantial genetic variability exists in certain regions of the virus which has made it possible to describe the existence of two groups of viruses,
- diagnosis of the viral infection remains difficult in spite of the possibility of detecting anti-HCV antibodies in the serum of patients. This is due to the existence of false positive results and to a delayed seroconversion following acute infection. Finally there are clearly cases where only the detection of the virus RNA makes it possible to detect the HCV infection while the serology remains negative.

These problems have important implications both with respect to diagnosis and protection against the virus.

The authors of the present invention have carried out the cloning and obtained the partial nucleotide sequence of a French isolate of HCV (called hereinafter HCV E1) from a blood donor who transmitted an active chronic hepatitis to a recipient. Comparison of the nucleotide sequences and the peptide sequences obtained with the respective sequences of the American and Japanese isolates showed that there was
- a high conservation of nucleic acids in the noncoding region of HCV E1,
- a high genetic variability in the structural regions called E1 and E2/NS1,
- a smaller genetic variability in the nonstructural region.

The present invention is based on new nucleotide and polypeptide sequences of the hepatitis C virus which have not been described in the abovementioned state of the art.

The subject of the present invention is thus a DNA sequence of HCV E1 comprising a DNA sequence chosen from the nucleotide sequences of at least 10 nucleotides between the following nucleotides (n); $n_{118}$ to $n_{138}$; $n_{177}$ to $n_{202}$; $n_{233}$ to $n_{247}$; $n_{254}$ to $n_{272}$ and $n_{272}$ to $n_{288}$ represented in the sequence ID SEQ No.2, and, $n_{156}$ to $n_{170}$; $n_{170}$ to $n_{217}$; $n_{267}$ to $n_{283}$ and $n_{310}$ to $n_{334}$ represented in the sequence ID SEQ No.3; as well as analogous nucleotide sequences resulting from degeneracy of the genetic code.

The subject of the invention is in particular the following nucleotide sequences: ID SEQ No.2, ID SEQ No.3 and ID SEQ No.4.

The oligonucleotide sequences may be advantageously synthesised by the Applied Bio System technique.

The subject of the invention is also a peptide sequence of HCV E1 comprising a peptide sequence chosen from the sequences of at least 7 amino acids between the following amino acids (aa): $aa_{58}$ to $aa_{66}$; $aa_{76}$ to $aa_{101}$ represented in the peptide sequence ID SEQ No.2; $aa_{49}$ to $aa_{78}$; $aa_{98}$ to $aa_{111}$; $aa_{123}$ to $aa_{133}$; $aa_{140}$ to $aa_{149}$ represented in the peptide sequence ID SEQ No.3; as well as homologous peptide sequences which do not induce modification of biological and immunological properties.

Preferably, the peptide sequence is chosen from the following amino acid sequences: $aa_{58}$ to $aa_{66}$; $aa_{76}$ to $aa_{101}$ represented in the peptide sequence ID SEQ No.2, $aa_{49}$ to $aa_{78}$; $aa_{98}$ to $aa_{111}$; $aa_{123}$ to $aa_{133}$ and $aa_{140}$ to $aa_{149}$ represented in the peptide sequence ID SEQ No.3.

Moreover, the peptide sequence is advantageously chosen from the peptide sequences ID SEQ No.2, ID SEQ No.3 and ID SEQ No.4.

The subject of the invention is also a nucleotide sequence encoding a peptide sequence as defined above.

Moreover, the subject of the invention is a polynucleotide probe comprising a DNA sequence as defined above.

The subject of the invention is also an immunogenic peptide comprising a peptide sequence as defined above.

The peptide sequences according to the invention can be obtained by conventional methods of synthesis or by the application of genetic engineering techniques comprising the insertion of a DNA sequence, encoding a peptide sequence according to the invention, into an expression vector such as a plasmid and the transformation of cells using this expression vector and the culture of these cells.

The subject of the invention is also plasmids or expression vectors comprising a DNA sequence encoding a peptide sequence as defined above as well as hosts transformed using this vector.

The preferred plasmids are those deposited with CNCM on Jun. 5, 1991 under the numbers I-1105, I-1106 and I-1107.

The subject of the invention is also monoclonal antibodies directed against a peptide sequence according to the invention or an immunogenic sequence of such a polypeptide.

The monoclonal antibodies according to the invention can be prepared according to a conventional technique. For this purpose, the polypeptides may be coupled, if necessary, to an immunogenic agent such as tetanus anatoxin using a coupling agent such as glutaraldehyde, a carbodiimide or a bisdiazotised benzidine.

The present invention also encompasses the fragments and the derivatives of monoclonal antibodies according to the invention. These fragments are especially $F(ab')_2$ fragments which can be obtained by enzymatic cleavage of the antibody molecules with pepsin, the Fab' fragments which can be obtained by reducing the disulphide bridges of the F(ab')$_2$ fragments, and the Fab fragments which can be obtained by enzymatic cleavage of the antibody molecules with papain in the presence of a reducing agent. These fragments, as well as the Fc fragments, can also be obtained by genetic engineering.

The derivatives of monoclonal antibodies are for example antibodies or fragments of these antibodies to which markers, such as a radioisotopes, are attached. The derivatives of monoclonal antibodies are also antibodies or fragments of these antibodies to which therapeutically active molecules are attached.

The subject of the invention is also an analytical kit for the detection of nucleotide sequences specific to the HVC E1 strain, comprising one or more probes as defined above.

The subject of the present invention is also an in vitro diagnostic process involving the detection of antigens specific to HCV E1, in a biological sample possibly containing the said antigens, in which, the biological sample is exposed to an antibody or an antibody fragment, as defined above; as well as a diagnostic kit for carrying out the process.

The subject of the invention is also an in vitro diagnostic process involving the detection of antibodies specific to HCV E1 in a biological sample possibly containing the said antibodies, in which a biological sample is exposed to an antigen containing an epitope corresponding to a peptide sequence, as well as a diagnostic kit for the detection of specific antibodies, comprising an antigen containing an epitope corresponding to a peptide sequence as defined above.

These procedures may be based on a radioimmunological method of the RIA, RIPA or IRMA type or an immunoenzymatic method of the WESTERN-BLOT type carried out on strips or of the ELISA type.

The subject of the invention is also a therapeutic composition comprising monoclonal antibodies or fragments of monoclonal antibodies or derivatives of monoclonal antibodies as defined above.

Advantageously, the monoclonal antibody derivatives are monoclonal antibodies or fragments of these antibodies attached to a therapeutically active molecule.

The subject of the invention is also an immunogenic composition containing an immunogenic sequence as defined above, optionally attached to a carrier protein, the said immunogenic sequence being capable of inducing protective antibodies or cytotoxic T lymphocytes. Anatoxins such as tetanus anatoxin may be used as carrier protein. Alternatively, immunogens produced according to the MAP (Multiple Antigenic Peptide) technique may also be used.

In addition to the immunogenic peptide sequence, the immunogenic composition may contain an adjuvant possessing immunostimulant properties.

The following are among the adjuvants which may be used: inorganic salts such as aluminium hydroxide, hydrophobic compounds or surface-active agents such as incomplete Freund's adjuvant, squalene or liposomes, synthetic polynucleotides, microorganisms or microbial components such as murabutide, synthetic artificial molecules such as imuthiol or levamisole, or alternatively cytokines such as interferons α, β, γ or interleukins.

The subject of the invention is also a process for assaying a peptide sequence as defined above, comprising the use of monoclonal antibodies directed against this peptide sequence.

The subject of the invention is also a process for preparing a peptide sequence as defined above, comprising the insertion of a DNA sequence, encoding the peptide sequence, into an expression vector, the transformation of cells using this expression vector and the culture of the cells.

The production of the DNA of the sequences of the HCV E1 strain will be described below in greater detail with reference to the accompanying figures in which:

FIG. 2 represents the comparison of the nucleotide sequence of HCV E1 (1), in the non-coding region, with the sequences of an American isolate (2) and two Japanese isolates: HCJ1 (3) and HCJ4 (4) respectively described in WO-A-90/14436 and by Okamoto et al. (12);

FIG. 3 represents the comparison of the nucleotide sequence of HCV E1 (1), in the region E1, with the sequences of an American isolate (HCVpt) (2) described in WO 90/14436 and three Japanese isolates: HCVJ-1 (3), HCJ1 (4) and HCJ4 (5) described in Takeuchi et al. (15); Okamoto et al. (12);

FIG. 4 represents the comparison of the aminoacid sequence, in the region E1, of HCV E1 (1) with the American isolate HCVpt (2) and the Japanese isolates: HCVJ1 (3), HCJ1 (4) and HCJ4 (5); the variable regions are boxed;

FIG. 5 represents the comparison of the nucleotide sequence, in the region E2/NS1, of HCV E1 (1) with the American isolate HCVpt (2) described in WO-A-90/14436 and the Japanese isolates HCJ1 (3), HCJ4 (4) and HCVJ1 (5) described by Okamoto et al. (12); Takeuchi et al. (15);

FIG. 6 represents a comparison of the aminoacid sequence, in the region E2/NS1, of HCV E1 (1) with the American isolate HCVpt (2) and the Japanese isolates HCJ1 (3), HCJ4 (4) and HCVJ1 (5); the variable regions are boxed;

FIG. 7 represents the hydrophilicity profile of HCV E1 in the region E2/NS1; the hydrophobic regions are located under the middle line;

FIG. 8 represents the comparison of the nucleotide sequence, in the region NS3/NS4, of HCV E1 (1) with the American isolate HCVpt (2) described in WO-A-90/14436 and the Japanese isolate HCVJ1 (3) described by Kubo et al. (7);

FIG. 9 represents the comparison of the aminoacid sequence, in the region NS3/NS4, of HCV E1 (1) with the American isolate HCVpt (2) and the Japanese isolate HCVJ1 (3).

I—PREPARATION OF THE NUCLEOTIDE SEQUENCES

1) Preparation of the HCV E1 RNA

The HCV E1 RNA was prepared as previously described in EP-A-0,318,216 from the serum of a French blood donor suffering from a chronic hepatitis, anti-HCV positive (anti-C100) (Kubo et al. (7)).

100 μl of serum were diluted in a final volume of 1 ml, in the following extraction buffer: 50 mM tris-HCl, pH.8, 1 mM EDTA, 100 mM NaCl, 1 mg/ml of proteinase K, and 0.5% SDS. After digestion with proteinase K for 1 h at 37° C., the proteins were extracted with one volume of TE-saturated phenol (10 mM Tris-HCl, pH.8, 1 mM EDTA). The aqueous phase was then extracted twice with one volume of phenol/chloroform (1:1) and once with one volume of chloroform. The aqueous phase was then adjusted to a final concentration of 0.2 M sodium acetate and the nucleic acids were precipitated by the addition of two volumes of ethanol. After centrifugation, the nucleic acids were suspended in 30 μl of DEPC-treated sterile distilled water.

2) Reverse Transcription and Amplification

Figure 1:
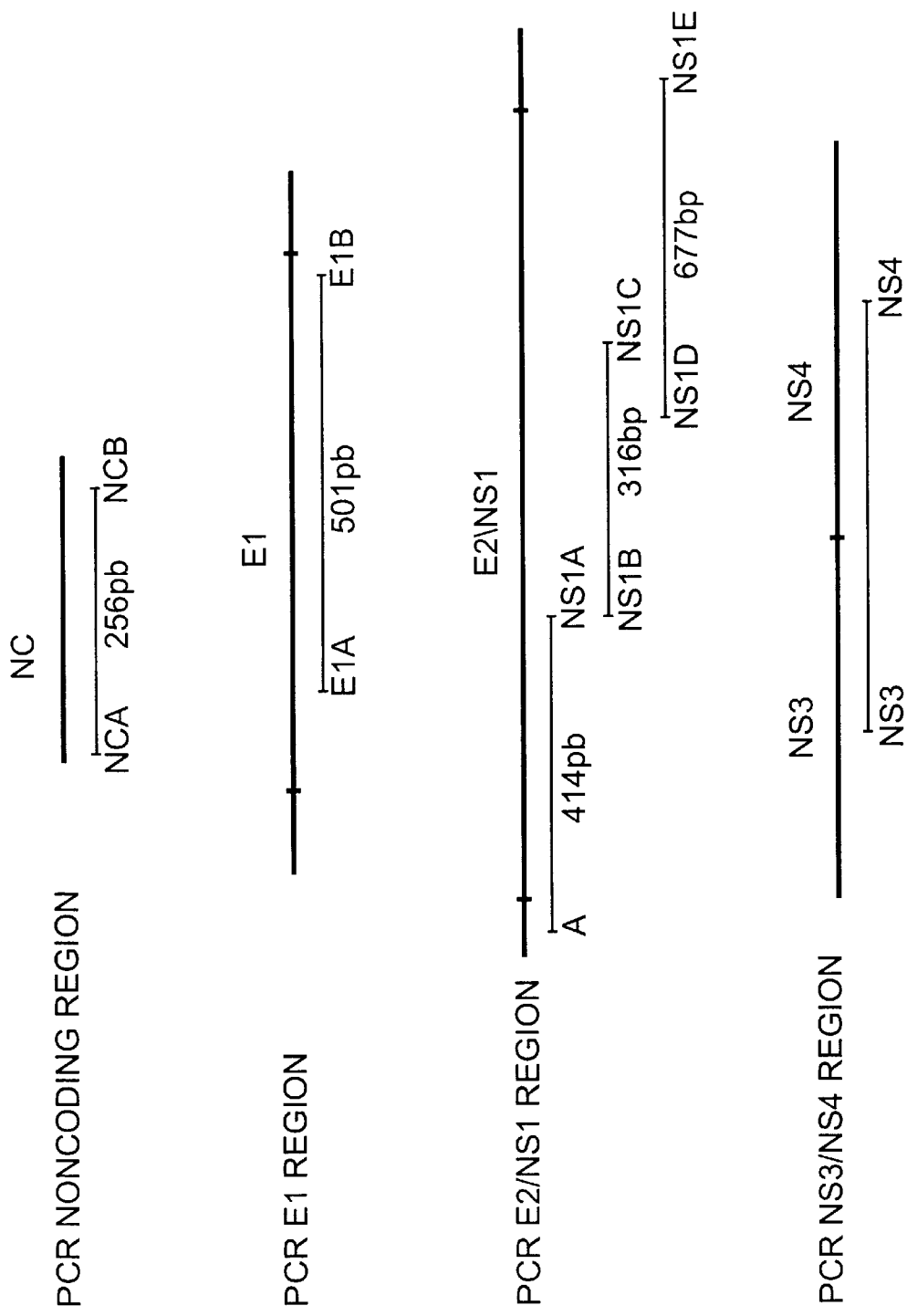
FIG. 1 represents the location of the amplified and sequenced HCV E1 regions.

A complementary DNA (cDNA) was synthesised using as primer either oligonucleotides specific to HCV, represented in Table I below, or a mixture of hexanucleotides not specific to HCV, and murine reverse transcriptase. A PCR (Polymerase Chain Reaction) was carried out over 40 cycles at the following temperatures: 94° C. (1 min), 55° C. (1 min), 72° C. (1 min), on the cDNA thus obtained, using pairs of primers specific to HCV (Table I below). Various HCV primers were made from the sequence of HCV prototype (HCVpt), isolated from a chronically infected chimpanzee (Bradley et al. (2); Alter et al. (1), EP-A-0,318,216). The nucleotide sequence of the 5' region of the E2/NS1 gene was obtained using a strategy derived from the sequence-independent single primer amplification technique (SISPA) described by Reyes et al. (13). It consists in ligating double-stranded adaptors to the ends of the DNA synthesised using an HCV-specific primer localised in 5' of the HCVpt sequence (primer NS1A in Table I). A semi-specific amplification is then carried out using an HCV-specific primer as well as a primer corresponding to the adaptor. This approach makes it possible to obtain amplification products spanning the 5' region of the primer used for the synthesis of the cDNA.

1) Nucleotide Sequence of HCV E1 in the Noncoding 5' Region

The amplified and sequenced noncoding 5' region of HCV E1 is called ID SEQ No.1. It corresponds to a 256-base pair (bp) fragment located in position −259 to −4 in HCVpt as described in WO-A-90/14436. Comparison of the HCV E1 sequence with those previously published shows a very high nucleic acid conservation (FIG. 2).

2) Nucleotide and Peptide Sequences of HCV E1 in the Structural Region

The nucleotide sequences probably correspond to two regions encoding the virus envelope proteins (currently designated as the E1 and E2/NS1 regions).

For the E1 region, the sequence obtained for HCV E1 corresponds to the 3' moiety of the gene. It has been called ID SEQ No.2. This 501-bp sequence is located in position 470 and 973 in the HCVpt sequence as described in WO-A-90/14436. Comparison of this sequence with those previously described shows a high genetic variability (FIG. 3). Indeed, depending on the isolates studied, a difference of 10 to 27% in nucleic acid composition and 7 to 20% in amino acid composition may be observed as shown in Table II below. Furthermore, comparison of the peptide sequence

TABLE I

Sequence of the primers and probes.

a) Primers[a]:

| | | |
|---|---|---|
| NS3 | (+) | 5' ACAATACGTGTGTCACC (3013–3029) |
| NS4 | (−) | 5' AAGTTCCACATATGCTTCGC (3955–3935) |
| NS1A | (−) | 5' TCCGTTGGCATAACTGATAG (83–64) |
| NS1B | (+) | 5' CTATCAGTTATGCCAACGGA (64–83) |
| NS1C | (−) | 5' GTTGCCCGCCCCTCCGATGT (380–361) |
| NS1D | (+) | 5' CCCAGCCCCGTGGTGGTGGG (183–202) |
| NS1E | (−) | 5' CCACAAGCAGGAGCAGACGC (860–841) |
| NCA | (+) | 5' CCATGGCGTTAGTATGAGT (−259—239) |
| NCB | (−) | 5' GCAGGTCTACGAGACCTC (−4—23) |
| E1A | (+) | 5' TTCTGGAAGACGGCGTGAAC (470–489) |
| E1B | (−) | 5' TCATCATATCCCATGCCATG (973–954) | b) probes[a]:

| | | |
|---|---|---|
| NS3/NS4 | (+) | 5' CCTTCACCATTGAGACAATCACGCTCCCCCAGGATGCTGT (3058–3097) |
| NS1 | (+) | 5' CTGTCCTGAGAGGCTAGCCAGCTGCCGACCCCTTACCGAT (5–44) |
| NS1B/C | (+) | 5' AGGTCGGGCGCGCCCACCTACAGCTGGGGTGAAAATGATA (210–248) |
| NC | (+) | 5' GTGCAGCCTCCAGGACCCCC (235—216) |
| E1 | (−) | 5' CTCGTACACAATACTCGAGT (646–627) |

[a]The nucleotide sequences and their locations correspond to the HCV prototype (HCVpt) (EP-A-0, 318, 216 and WO-A-90/14436).

3) Cloning and Sequencing

The amplification products were cloned into M13 mp19 or into the bacteriophage lambda gt 10 as described by Thiers et al. (17). The probes used for screening the DNA sequences are represented in Table I above. The nucleotide sequence of the inserts was determined by the dideoxynucleotide-based method described by Sanger et al., (14).

II—STUDY OF THE NUCLEOTIDE SEQUENCES OF THE FRENCH isolate (HCV E1)

The location of the various amplification products which made it possible to obtain the nucleotide sequence of the HCV E1 isolate in nonstructural and structural regions as well as in the noncoding region of the virus, is schematically represented in FIG. 1.

reveals the existence of two hypervariable regions which are boxed in FIG. 4.

Figure 5A:
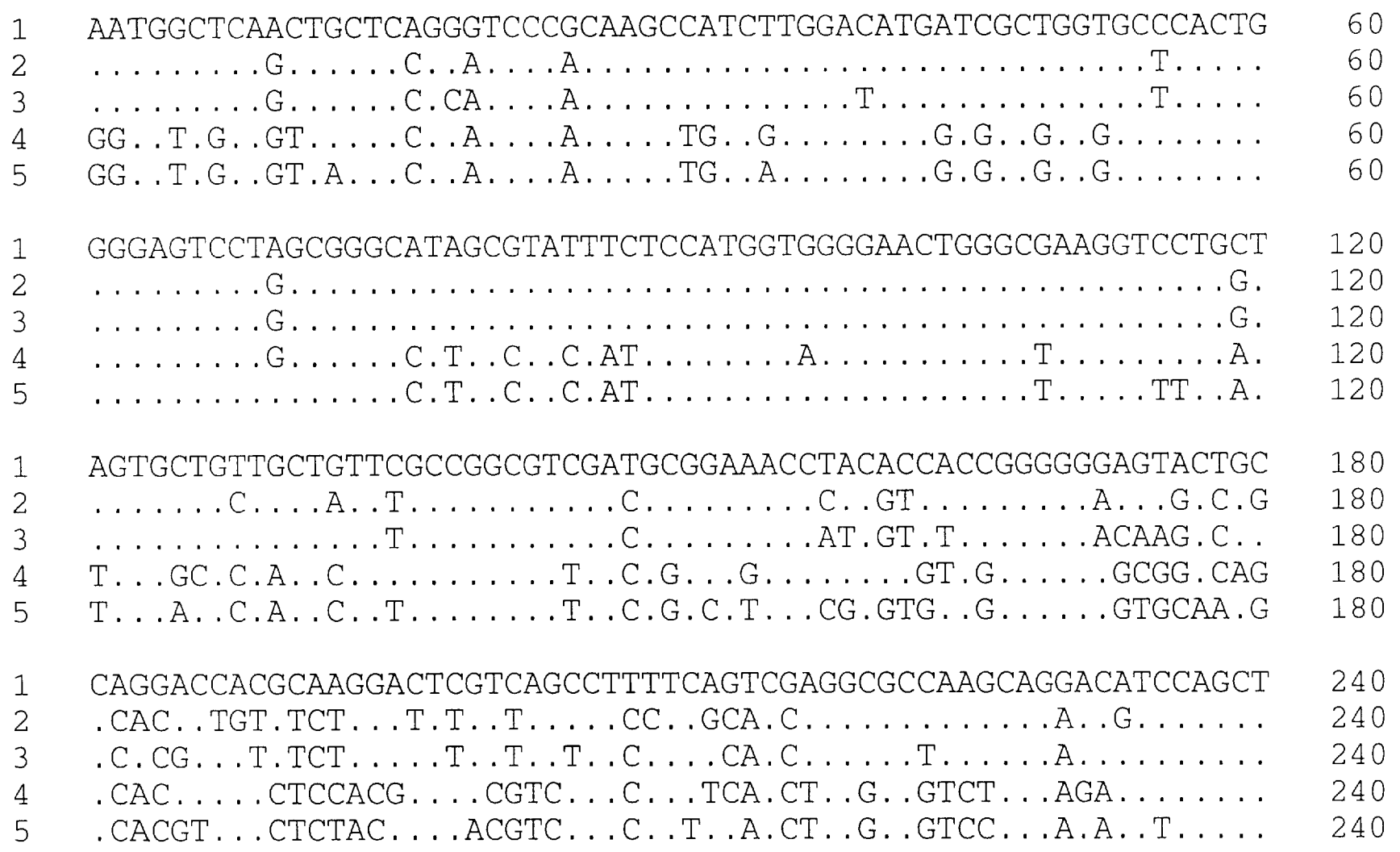
Figure 6A:
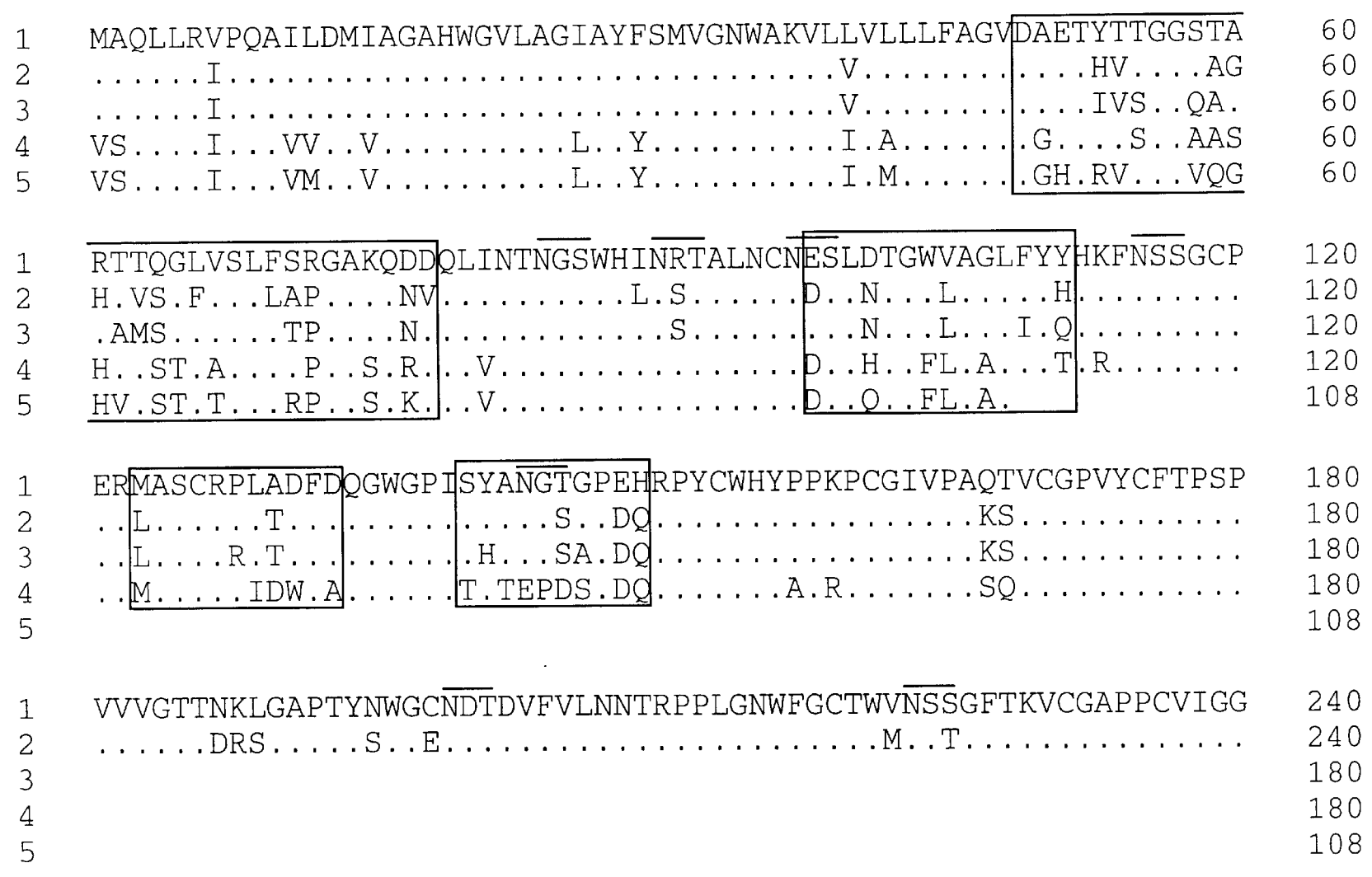
Figure 7:
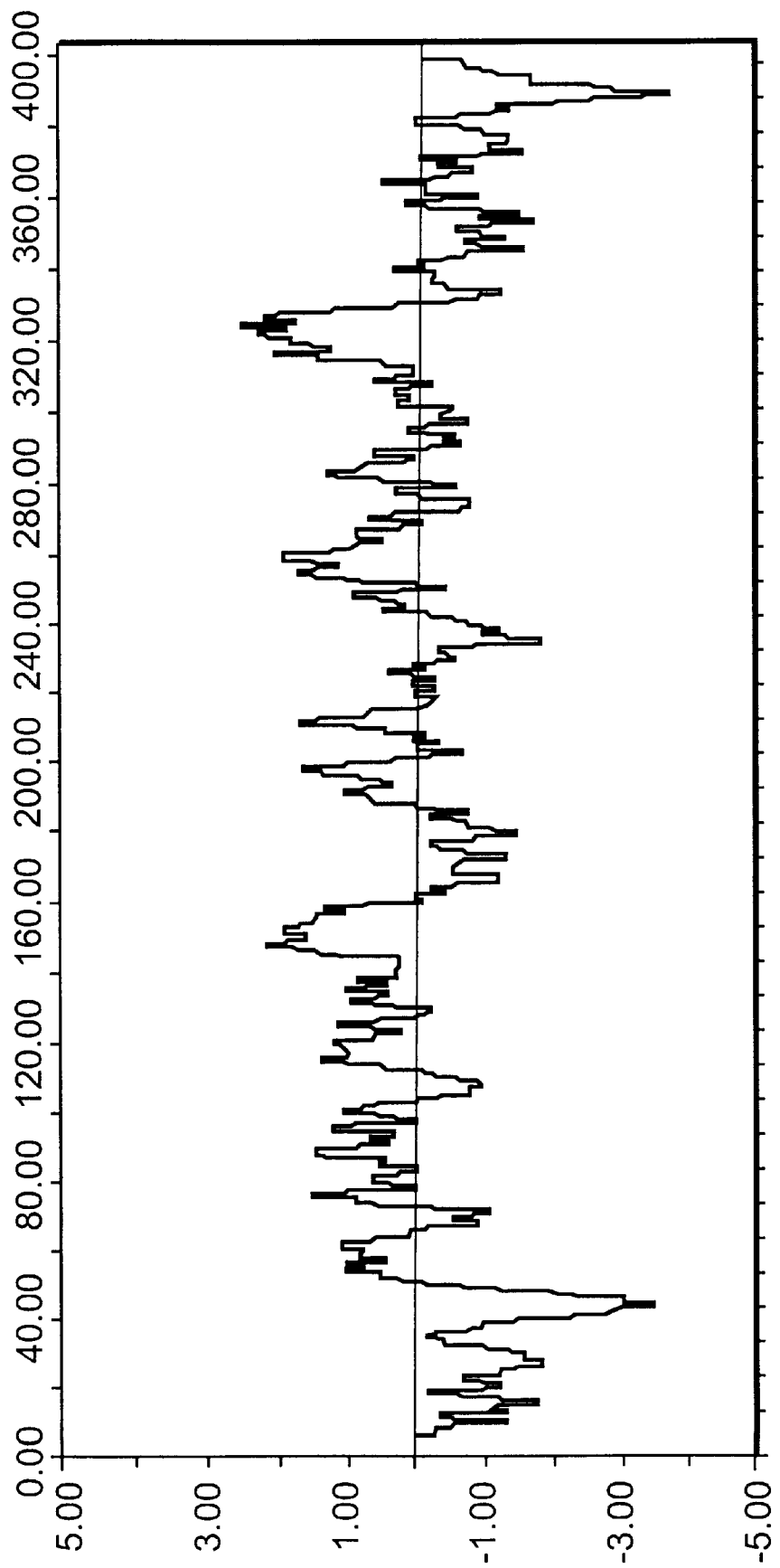

For the E2/NS1 region, the HVC E1 sequence data were obtained from three overlapping amplification products (FIG. 1). The consensus sequence thus obtained (1210 bp) contains the entire E2/NS1 gene and was called ID SEQ No.3. The sequence of the E2/NS1 region of HCV E1 is situated in position 999 and 2209 compared with the HCVpt sequence described in WO-A-90/14436. Comparison of the HCV E1 sequences with the isolates previously described shows a difference of 13 to 33% in the case of nucleic acids and 11 to 30% in the case of amino acids (FIG. 5 and 6, Table II). The highest variability is observed in 5' of the E2/NS1 gene (FIG. 5). Comparison of amino acids shows the existence of four hypervariable regions which are boxed in FIG. 6. The hydrophilicity profile of the E2/NS1 region (Kyte and Dolittle, (9)) is given in FIG. 7. A hydrophilic region flanked by two hydrophobic regions are observed. Both hydrophobic regions probably correspond to the signal sequence as well as to the transmembrane segment. Finally, the central region has ten potential glycolisation [sic] sites (N-X-T/S), which are conserved in the various isolates (FIG. 6).

3) Nucelotide and Peptide Sequence of HCV E1 in the Nonstructural Region

The sequence data for HCV E1 in the nonstructural region correspond to the 3' and 5' terminal parts of the NS3 and NS4 genes respectively (FIG. 1). The sequence obtained for HCV E1 (943 bp) is located in position 4361 to 5303 in the HCVpt sequence and was called ID SEQ No.4. The sequence homology is 95% with the HCVpt isolate and 78.6% with a Japanese isolate (FIG. 8, Table II above). In the case of the comparison of amino acids, a homology of 98% and 93% was observed with the HCVpt and Japanese isolates respectively (FIG. 8, Table II above).

Thus, comparison of the nucleotide sequence of the HCV E1 isolate with that of the American and Japanese isolates shows that the French isolate is different from the isolates described above. It reveals the existence of highly variable regions in the envelope proteins. The variability of the nonstructural region studied is lower. Finally, the noncoding 5' region shows a high conservation.

These results have implications both for diagnosis and prevention of HVC.

As far as diagnosis is concerned, definition of the hypervariable regions and of the conserved regions can lead to:

the definition of synthetic peptides which allow the expression of epitopes specific to the various HCV groups.

For the envelope protein E1, peptides for the determination of type-specific epitopes are advantageously defined in a region between amino acids 75 to 100 (FIG. 4). Likewise, for the protein E2/NS1, peptides allow [sic] characterisation of specific epitopes are synthesised in regions preferably between amino acids 50 and 149, (FIG. 6).

The expression of all or part of the cloned sequences, in particular clones corresponding to the envelope regions of the virus, make it possible to obtain new antigens for the development of diagnostic reagents and for the production of immunogenic compositions. Finally, the preparation of a substantial part of the nucleotide sequence of this isolate allows the production of the entire length of complementary DNA which can be used for a better understanding of the mechanisms of the viral infection and also for diagnostic and preventive purposes.

TABLE II

Difference in nucleic acids (n.a.) and amino acids (a.a.) between the French isolate (HCV E1) and the American (HCVpt) and japanese (HCVJ1, HCJ1, HCJ4) isolates.

|  |  | HCVpt | HCVJ1 | HCJ1 | HCJ4 |
|---|---|---|---|---|---|
| HCVE1 E1 | n.a. | 10.6 | 27.3 | 10.4 | 26.5 |
|  | a.a. | 7.2 | 19.9 | 8.4 | 20.5 |
| HCVE1 E2/NS1 | n.a. | 12.8% | 33.2% | 14.5% | 29.8% |
|  | a.a | 12.2% | 29.7% | 15.6% | 26.1% |
| HCVE1 NS3/NS4 | n.a. | 5.2% | 21.4% |  |  |
|  | a.a. | 2.2% | 6.9% |  |  |

REFERENCES

1. Alter, H. J., Purcell, R. H., Shib, J. W., Melpolder, J. C., Houghton, M., Choo, Q. -L. & Kuo, G. (1989). Detection of antibody to hepatitis C virus in prospectively followed transfusion recipients with acute and chronic Non-A, Non-B hepatitis. New England Journal of Medicine 321, 1494–1500.
2. Bradley, D. W., Cook, E. H., Maynard, J. E., McCaustland, K. A., Ebert, J. W., Dolana, G. H., Petzel, R. A., Kantor, R. J., Heilbrunn, A., Fields, H. A. & Murphy, B. L. (1979). Experimental infection of chimpanzees with antihemophilic (factor VIII) materials: recovery of virus-like particles associated with Non-A, Non-B hepatitis. Journal of Medical Virology 3, 253–269.
3. Choo, Q. -L., Kuo, G., Weiner, A. J., Overby, L. R., Bradley, D. W. & Houghton, M. (1989). Isolation of a cDNA clone derived from a blood-borne Non-A, Non-B viral hepatitis genome. Science 244, 359–362.
4. Enomoto, N., Takada, A., Nakao, T. & Date, T. (1990). There are two major types of hepatitis C virus in Japan. Biochemical and Biophysical Research Communications 170, 1021–1025.
5. Hopf, U., Möbller, B., Kuther, D., Stemerowicz, R., Lobeck, H., Lüdtke-Handjery, A., Walter, E., Blum, H. E., Roggendorf, M. & Deinhardt, F. (1990). Long-term follow-up of post transfusion and sporadic chronic hepatitis Non-A, Non-B and frequency of circulating antibodies to hepatitis C virus (HCV). Journal of Hepatology 10, 69–76.
6. Kato, N., Hijakata, M., Ootsuyama, Y., Nakagawa, M., Ohkoshi, S., Sugimura, T. & Shimotohno, K. (1990). Molecular cloning of the human hepatitis C virus genome from Japanese patients with Non-A, Non-B hepatitis. Proceedings of the National Academy of Sciences, U.S.A. 87, 9524–9528.
7. Kubo, Y., Takeuchi, K., Boonmar, S., Katayama, T., Choo, Q. -L., Kuo, G., Weiner, A.J., Bradley D. W., Houghton, M., Saito, I. & Miyamura, T. (1989). A cDNA fragment of hepatitis C virus isolated from an implicated donor of post-transfusion Non-A, Non-B hepatitis in Japan. Nucleic Acids Research 17, 10367–10372.
8. Kuo, G., Choo, Q. -L., Alter, H. J., Gitnick, G. L., Redeker, A. G., Purcell, R. H., Miyamura, T., Dienstag, J. L., Alter, M. J., Stevens, C. E., Tegtmeier, G. E., Bonino, F., Colombo, M., Lee, W. S., Kuo, C., Berger, K., Shuster, J. R., Overby, L. R., Bradley, D. W. & Houghton, M. (1989). An assay for circulating antibodies to a major etiologic virus of human Non-A, Non-B hepatitis. Science 244, 362–364.
9. Kyte, W. & Doolittle, R. F. (1982). A simple method for displaying the hydropathic of a protein. Journal of Molecular Biology 157, 105–132.
10. Miller, R. H. & Purcell, R. H. (1990). Hepatitis C virus shares amino acid sequence similarity with pestiviruses and flaviviruses as well as members of two plant virus super groups. Proceedings of the National Academy of Sciences, U.S.A. 87, 2057–2061.
11. Miyamura, T., Saito, T., Katayama, T., Kikuchi, S., Tateda, A., Houghton, M., Choo, Q. -L. & Kuo, G. (1990). Detection of antibody against antigen expressed by molecularly cloned hepatitis C virus cDNA: application to diagnosis and blood screening for posttransfusion hepatitis. Proceedings of the National Academy of Sciences, U.S.A. 87, 983–987.
12. Okamoto, H., Okada, S., Sugiyama, Y., Yotsumoto, S., Tanaka, T., Yoshizawa, H., Tsuda, F., Miyakawa, Y. &

Mayumi, M. (1990). The 5' terminal sequence of the hepatitis C virus genome. Japanese Journal of Experimental Medicine 60, 167–177.

13. Reyes, G. R., Purdy, M. A., Kim, J. P., Luk, K. -C., Young, L. M., Fry, K. E. & Bradley, D. W. (1990). Isolation of a cDNA from the virus responsible for enterically transmitted Non-A, Non-B hepatitis. Science 247, 1335–1339.

14. Sanger, F. S., Nicklen, S. & Coulsen, A. R. (1977). DNA sequencing with chain terminating inhibition. Proceedings of the National Academy of Sciences, U.S.A. 74, 5463–5467.

15. Takeuchi, K., Boonmar, S., Kubo, Y., Katayama, T., Harada, H., Ohbayashi, A., Choo, Q., -L., Houghton, M., Saito, I. & Miyamura, T. (1990a). Hepatitis C viral cDNA clones isolated from a healthy carrier donor implicated in post-transfusion Non-A, Non-B hepatitis. Gene 91 (2), 287–291.

16. Takeuchi, K., Kubo, Y., Boonmar, S., Watanabe, Y., Katayama, T., Choo, Q. -L., Kuo, G., Houghton, M., Saito, I. & Miyamura, T. (1990b). Nucleotide sequence of core and envelope genes of the hepatitis C virus genome derived directly from human healthy carriers. Nucleic Acids Research 18, 4626.

17. Thiers, V., Nakajima, E. N., Kremsdorf, D., Mack, D., Schellekens, H., Driss, F., Goude, A., Wands, J., Sninsky, J., Tiollais, P. & Brechot, C. (1988). Transmission of hepatitis B from hepatitis B seronegative subjects. Lancet ii, 1273–1276

| Symbols for the amino acids | | |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

What is claimed is:

1. A plasmid selected from the group consisting of plasmids deposited at C.N.C.M. under accession numbers I-1105, I-1106, and I-1107.

2. A recombinant DNA molecule comprising
   a nucleotide sequence of HCV E1 contained in a plasmid selected from the group consisting of plasmids deposited at C.N.C.M. under accession numbers I-1105, I-1106, and I-1107, and
   a nucleotide sequence encoding a peptide, wherein said peptide is an amino acid (aa) sequence selected from the group consisting of:
   $aa_{58}$ to $aa_{66}$ of SEQ ID NO:3;
   $aa_{49}$ to $aa_{78}$ of SEQ ID NO:5;
   $aa_{123}$ to $aa_{133}$ of SEQ ID NO:5;
   SEQ ID NO:3;
   SEQ ID NO:5; and
   SEQ ID NO:7.

3. A purified form of the genome of HCV E1 contained in a plasmid selected from the group consisting of plasmids deposited at C.N.C.M. under accession numbers I-1105, I-1106, and I-1107.

* * * * *